United States Patent
Burns et al.

(10) Patent No.: US 9,802,966 B2
(45) Date of Patent: *Oct. 31, 2017

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Bin Liu, Plainsboro, NJ (US); Daniel McGarry, Malvern, PA (US); Daniel C. Pevear, Downingtown, PA (US); Robert E. Lee Trout, Collegeville, PA (US)

(73) Assignee: VENATORX PHARMACEUTICALS, INC., Malvern, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/333,049

(22) Filed: Oct. 24, 2016

(65) Prior Publication Data

US 2017/0107239 A1   Apr. 20, 2017

Related U.S. Application Data

(63) Continuation of application No. 14/737,323, filed on Jun. 11, 2015, now Pat. No. 9,511,142.

(60) Provisional application No. 62/010,974, filed on Jun. 11, 2014.

(51) Int. Cl.
*A61K 31/69* (2006.01)
*A61K 45/06* (2006.01)
*C07F 5/02* (2006.01)

(52) U.S. Cl.
CPC .............. *C07F 5/025* (2013.01); *A61K 31/69* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,427,690 A | 1/1984 | Cole et al. | |
| 7,271,186 B1 | 9/2007 | Shoichet et al. | |
| 8,680,136 B2 | 3/2014 | Hirst et al. | |
| 8,912,169 B2 | 12/2014 | Burns et al. | |
| 9,040,504 B2 | 5/2015 | Burns et al. | |
| 9,101,638 B2 | 8/2015 | Reddy et al. | |
| 9,376,454 B2 | 6/2016 | Burns et al. | |
| 9,403,850 B2 | 8/2016 | Burns et al. | |
| 9,422,314 B2 | 8/2016 | Burns et al. | |
| 9,511,142 B2* | 12/2016 | Burns et al. ............ | A61K 31/69 |
| 2010/0056478 A1 | 3/2010 | Desarbre et al. | |
| 2010/0120715 A1 | 5/2010 | Burns et al. | |
| 2010/0286092 A1 | 11/2010 | Burns et al. | |
| 2010/0292185 A1 | 11/2010 | Burns et al. | |
| 2010/0317621 A1 | 12/2010 | Burns et al. | |
| 2011/0294777 A1 | 12/2011 | Blizzard et al. | |
| 2012/0040932 A1 | 2/2012 | Hirst et al. | |
| 2015/0361106 A1 | 12/2015 | Burns et al. | |
| 2015/0361107 A1 | 12/2015 | Trout | |
| 2015/0361108 A1 | 12/2015 | Burns et al. | |
| 2016/0024121 A1 | 1/2016 | Burns et al. | |
| 2016/0264598 A1 | 9/2016 | Burns et al. | |
| 2016/0304539 A1 | 10/2016 | Burns et al. | |

FOREIGN PATENT DOCUMENTS

| | | |
|---|---|---|
| WO | WO-2005004799 A2 | 1/2005 |
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2012021455 A1 | 2/2012 |
| WO | WO-2013053372 A1 | 4/2013 |
| WO | WO-2013122888 A2 | 8/2013 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2015171398 A1 | 11/2015 |
| WO | WO-2015171430 A1 | 11/2015 |
| WO | WO-2015179308 A1 | 11/2015 |
| WO | WO-2016003929 A1 | 1/2016 |

OTHER PUBLICATIONS

Co-pending U.S. Appl. No. 15/366,769, filed Dec. 1, 2016.
Patani et al. Bioisosterism: A Rational Approach in Drug Design. Chemical Reviews 96:3147-3176 (1996).
Bodner Research Web. The Chemistry of the Halogens. Available from http://web.archive.org/web/20090414155348/http://chemechem/topicreview/bp/ch10/group3.php (2009).
Bundgaard. Design of Prodrugs. Elsevier. Chapter 1. pp. 1-3 (1985).
Burns et al. CAPLUS AN 2014-1130723 (2014).
Co-pending U.S. Appl. No. 15/212,959, filed Jul. 18, 2016.
Co-pending U.S. Appl. No. 15/261,359, filed Sep. 9, 2016.
Eidam et al. Design, synthesis, crystal structures, and antimicrobial activity of sulfonamide boronic acids as β-lactamase inhibitors. J. Med. Chem. 53(21):7852-7863 (2010).
Ettmayer et al. Lessons Learned from Marketed and Investigational Prodrugs. J Medicinal Chem 47(10):2393-2404 (2004).
Han. Targeted Prodrug Design to Optimize Drug Delivery. AAPS Pharmsci. 2(1)Article 6:1-11 (2000).
Isomer. https://en.wikipedia.org/wiki/Isomer (2015).
Lima et al. Bioisosterism: A Useful Strategy for Molecular Modification and Drug Design. Current Medicinal Chemistry 12:23-49 (2005).
Morandi et al. Structure-based optimization of cephalothin-analogue boronic acids as β-lactamase inhibitors. Bioorg. Med. Chem. 16(3):1195-1205 (2008) (Epub: Nov. 7, 2007).

(Continued)

*Primary Examiner* — Zinna Northington Davis
(74) *Attorney, Agent, or Firm* — Wilson Sonsini Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

20 Claims, No Drawings

(56) References Cited

OTHER PUBLICATIONS

Ness et al. Structure-based design guides the improved efficacy of deacylation transition state analogue inhibitors of TEM-1 β-lactamase. Biochemistry 39(18):5312-5321 (2000).
PCT/US2013/073428 International Preliminary Report on Patentability dated Jun. 18, 2015.
PCT/US2013/073428 International Search Report dated Apr. 25, 2014.
PCT/US2014/011144 International Preliminary Report on Patentability dated Jul. 23, 2015.
PCT/US2014/011144 International Search Report dated May 12, 2014.
PCT/US2014/026727 International Preliminary Report on Patentability dated Sep. 24, 2015.
PCT/US2014/026727 International Search Report and Written Opinion dated Jul. 25, 2014.
PCT/US2015/035407 International Search Report and Written Opinion dated Oct. 20, 2015.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Testa. Prodrug research: futile or fertile? Biochem. Pharm. 68:2097-2106 (2004).
U.S. Appl. No. 14/152,916 Office Action dated Aug. 29, 2014.
U.S. Appl. No. 14/649,527 Office Action dated Nov. 9, 2015.
U.S. Appl. No. 14/693,318 Office Action dated Sep. 1, 2015.
U.S. Appl. No. 14/737,323 Office Action dated Mar. 18, 2016.
U.S. Appl. No. 14/759,853 Office Action dated Dec. 11, 2015.
Weston et al. Structure-based enhancement of boronic acid-based inhibitors of AmpC β-lactamase. J. Med. Chem. 41(23):4577-4586 (1998).
Bacterial Infection 101. Available at http://www.onhealth.com/content/I/bacterial_infections (34 pgs) (2017).
Definition of Quinoxaline from PubChem. http://pubchem.ncbi.nlm.nih.gov/compund/quinoxaline#section=information-sources. (24 pgs) (2005).
Definition of Quinoxaline from Wikipedia. http://en.wikipedia.org/wiki/Quinoxaline (3 pgs.) (2016).
Ishikawa et al. Synthesis and antimicrobial activity of 2,3-bis(bromomethyl)quinoxaline derivatives. Bioorg Chem 41-42:1-5 (2012).
Pub Chem Substance Record for SID 197433672. htttps://pubchem.ncbi.nim.nih/substance/197433672. Created Aug. 18, 2014. Retrieved Jan. 10, 2017 (5 pgs).
U.S. Appl. No. 14/773,717 Office Action dated Feb. 27, 2017.
U.S. Appl. No. 14/773,717 Office Action dated Jun. 8, 2017.
U.S. Appl. No. 15/194,433 Office Action dated Feb. 9, 2017.
U.S. Appl. No. 15/212,959 Office Action dated Mar. 23, 2017.
U.S. Appl. No. 90/013,866 Ex Parte Reexam Office Action dated Apr. 20, 2017.
Isomer. https://en.wikipedia.org/wiki/Isomer (5 pgs) (2017).

\* cited by examiner

BETA-LACTAMASE INHIBITORS

CROSS-REFERENCE TO RELATED APPLICATIONS

This application is a continuation of U.S. patent application Ser. No. 14/737,323, filed Jun. 11, 2015, which claims the benefit of U.S. Provisional Application Ser. No. 62/010,974, filed Jun. 11, 2014, all of which are hereby incorporated by reference in its entirety.

STATEMENT AS TO FEDERALLY SPONSORED RESEARCH

This invention was made with the support of the United States government under Contract numbers R44AI096613 by National Institutes of Health (NIH), and R43AI096679 by National Institutes of Health (NIH). The government has certain rights in the invention.

FIELD OF INVENTION

The present invention relates to boron-containing compounds, compositions, preparations and their use as inhibitors of beta-lactamase enzymes and as antibacterial agents.

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) are widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community. Currently available beta-lactamase inhibitors (for example, clavulanic acid and tazobactam) are poorly active against the diversity of beta-lactamase enzymes (both serine- and metallo-based) now emerging clinically. There is an urgent need for new beta-lactamase inhibitors with broadened enzyme spectrum.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections.

In one aspect, provided herein are compounds of Formula I or pharmaceutically acceptable salts, tautomers, or N-oxides thereof:

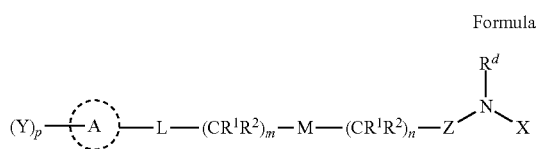

Formula (I)

wherein:
L is a bond, —C($R^1R^2$)—, —C(=O)—, or =C($R^1$)—;
M is a bond, —O—, —S—, —S(O)—, —S(O)$_2$—, or —N($R^4$)—;
m is 0, 1, or 2;
n is 0, 1, 2, or 3;
p is 0, 1, 2, 3, or 4;
Z is —C(=O)—, —C(=S), or —S(O)$_2$—;
A is CycA, ArA or HetA, wherein
  CycA is an optionally substituted 3-10 membered non-aromatic carbocycle, wherein an optional olefin functionality of the non-aromatic carbocycle is not directly attached to an oxygen, sulfur, or nitrogen substituent;
  ArA is an aromatic or heteroaromatic ring system optionally substituted with one or more substituents selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, and —$SR^{10}$;
  HetA is an optionally substituted non-aromatic heterocyclic ring system;
each $R^1$ and $R^2$ is independently selected from the group consisting of hydrogen, fluoro, chloro, bromo, optionally substituted $C_1$-$C_6$ alkyl, optionally substituted $C_3$-$C_6$ cycloalkyl, —OH, —$OR^{10}$, —$SR^{10}$, and —$NR^4R^5$,
  or $R^1$ and $R^2$ taken together form an oxo, oxime, or an optionally substituted carbocycle or optionally substituted heterocycle with the carbon to which they are attached;
each $R^d$, $R^4$, and $R^5$ is independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
  or $R^4$ and $R^5$ taken together form an optionally substituted heterocycle with the nitrogen to which they are attached;
each $R^{10}$ is independently selected from the group consisting of optionally substituted $C_1$-$C_6$ alkyl and optionally substituted $C_3$-$C_6$ cycloalkyl;
each Y is independently a group comprising 1-50 non-hydrogen atoms selected from the group consisting of C, N, O, S, and P; and
X is

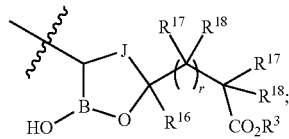

J is a 1-4 atom alkylene or 1-4 atom alkenylene, optionally substituted by one or more substituents selected from the group consisting of Cl, F, CN, $CF_3$, —$R^{19}$, —OR$^{19}$, —C(=O)NR$^{19}$R$^{20}$, and —C(=O)OR$^{19}$, wherein said 1-4 atom alkylene or 1-4 atom alkenylene is optionally fused to an optionally substituted aryl, optionally substituted heteroaryl, optionally substituted carbocyclyl, or optionally substituted heterocyclyl;

R$^3$ is selected from the group consisting of R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one;

each R$^{30}$ is independently —CH$_2$—, —CH(CH$_3$)—, —C(CH$_3$)$_2$—, or optionally substituted 1,1'-cyclopropylene;

R$^{31}$ is selected from the group consisting of optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocycloalkyl, optionally substituted aryl, optionally substituted heteroaryl, optionally substituted alkylcycloalkyl, optionally substituted alkylheterocycloalkyl, optionally substituted alkylaryl, and optionally substituted alkylheteroaryl;

each q is independently 2, 3, 4, 5, or 6;

R$^{16}$ is selected from a group consisting of H, —C$_1$-C$_9$alkyl, —C$_2$-C$_9$alkenyl, —C$_2$-C$_9$alkynyl, carbocyclyl, —C$_1$-C$_9$alkylR$^{21}$, —C$_2$-C$_9$alkenylR$^{21}$, —C$_2$-C$_9$alkynylR$^{21}$, carbocyclylR$^{21}$, —C(=O)OR$^{19}$, —C$_1$-C$_9$alkylC(=O)OR$^{19}$, —C$_2$-C$_9$alkenylC(=O)OR$^{19}$, —C$_2$-C$_9$alkynylC(=O)OR$^{19}$, carbocyclylC(=O)OR$^{19}$, or alternatively:

(i) R$^{16}$ and an R$^{17}$ are taken together with the atoms to which they are attached to form a substituted or unsubstituted carbocyclyl or substituted or unsubstituted heterocyclyl, (ii) R$^{16}$ and a carbon atom in J are taken together with intervening atoms to form a substituted or unsubstituted carbocyclyl or substituted or unsubstituted heterocyclyl, or (iii) R$^{16}$ is absent when the carbon to which it is attached is a ring atom in an aryl or heteroaryl ring;

each R$^{17}$ is independently selected from a group consisting of H, halo, —C$_1$-C$_9$alkyl, —C$_2$-C$_9$alkenyl, —C$_2$-C$_9$alkynyl, NR$^{19}$R$^{20}$, —OR$^{19}$, —C$_1$-C$_9$alkylC(=O)OR$^{19}$, —C$_2$-C$_9$alkenylC(=O)OR$^{19}$, —C$_2$-C$_9$alkynylC(=O)OR$^{19}$, carbocyclylC(=O)OR$^{19}$, or independently:

(i) R$^{16}$ and an R$^{17}$ are taken together with the atoms to which they are attached to form a substituted or unsubstituted carbocyclyl or substituted or unsubstituted heterocyclyl, (ii) R$^{17}$ and an R$^{18}$ are taken together with the atoms to which they are attached to form a substituted or unsubstituted carbocyclyl or substituted or unsubstituted heterocyclyl, (iii) an R$^{17}$ and a carbon atom in J are taken together with intervening atoms to form a substituted or unsubstituted carbocyclyl or substituted or unsubstituted heterocyclyl;

each R$^{18}$ is independently selected from a group consisting of H, halo, —C$_2$-C$_9$alkenyl, —C$_2$-C$_9$alkynyl, NR$^{19}$R$^{20}$, —OR$^{19}$, —C$_1$-C$_9$alkylC(=O)OR$^{19}$, —C$_2$-C$_9$alkenylC(=O)OR$^{19}$, —C$_2$-C$_9$alkynylC(=O)OR$^{19}$, carbocyclylC(=O)OR$^{19}$, or independently:

(i) an R$^{17}$ and an R$^{18}$ are taken together with the atoms to which they are attached to form a substituted or unsubstituted carbocyclyl or substituted or unsubstituted heterocyclyl, (ii) a geminal R$^{17}$ and R$^{18}$ together form —C$_2$-C$_9$alkenylC(=O)OR$^{19}$, or (iii) each R$^{18}$ attached to a ring atom forming part of a substituted or unsubstituted aryl is absent;

each R$^{19}$ is independently selected from a group consisting of H, —C$_1$-C$_9$alkyl, —C$_2$-C$_9$alkenyl, —C$_2$-C$_9$alkynyl, carbocyclyl, —C$_1$-C$_9$alkylR$^{21}$, —C$_2$-C$_9$alkenylR$^{21}$, —C$_2$-C$_9$alkynylR$^{21}$, carbocyclylR$^{21}$, substituted or unsubstituted aryl, substituted or unsubstituted heteroaryl, substituted or unsubstituted carbocyclyl, and substituted or unsubstituted heterocyclyl;

each R$^{20}$ is independently selected from a group consisting of H, —C$_1$-C$_9$alkyl, —OR$^{19}$, —CH(=NH), —C(=O)OR$^{19}$, substituted or unsubstituted aryl, substituted or unsubstituted heteroaryl, substituted or unsubstituted carbocyclyl, and substituted or unsubstituted heterocyclyl;

each R$^{21}$ is independently selected from a group consisting of substituted or unsubstituted aryl, substituted or unsubstituted heteroaryl, substituted or unsubstituted carbocyclyl, and substituted or unsubstituted heterocyclyl; and r is 0 or 1, wherein each —C$_1$-C$_9$alkyl, —C$_2$-C$_9$alkenyl, and —C$_2$-C$_9$alkynyl is independently optionally substituted.

In some embodiments is a compound of Formula I, wherein X is

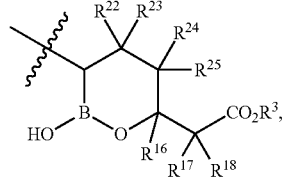

and R$^{22}$, R$^{23}$, R$^{24}$, and R$^{25}$ are independently H, Cl, F, CN, CF$_3$, —R$^{19}$, —OR$^{19}$, —C(=O)NR$^{19}$R$^{20}$, or —C(=O)OR$^{19}$. In some embodiments is a compound of Formula I, wherein X is

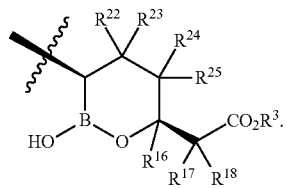

In some embodiments is a compound of Formula I, wherein X is

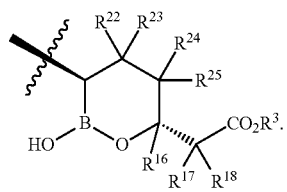

In some embodiments is a compound of Formula I, wherein $R^{22}$, $R^{23}$, $R^{24}$, and $R^{25}$ are H.

In some embodiments is a compound of Formula I, wherein X is

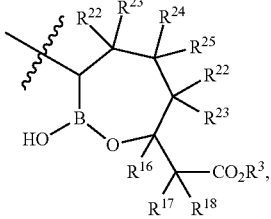

and each $R^{22}$, $R^{23}$, $R^{24}$, and $R^{25}$ are independently H, Cl, F, CN, CF$_3$, —$R^{19}$, —$OR^{19}$, —C(=O)NR$^{19}$R$^{20}$, or —C(=O)OR$^{19}$. In some embodiments is a compound of Formula I, wherein X is

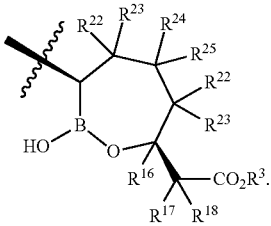

In some embodiments is a compound of Formula I, wherein X is

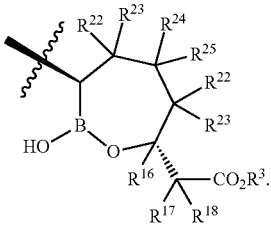

In some embodiments is a compound of Formula I, wherein $R^{22}$, $R^{23}$, $R^{24}$, and $R^{25}$ are H.

In some embodiments is a compound of Formula I, wherein X is

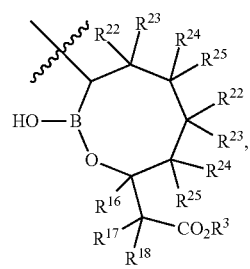

and each $R^{22}$, $R^{23}$, $R^{24}$, and $R^{25}$ are independently H, Cl, F, CN, CF$_3$, —$R^{19}$, —$OR^{19}$, —C(=O)NR$^{19}$R$^{20}$, or —C(=O)OR$^{19}$. In some embodiments is a compound of Formula I, wherein X is

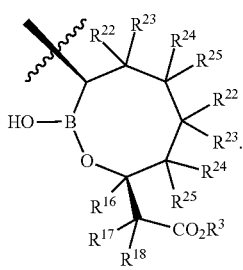

In some embodiments is a compound of Formula I, wherein X is

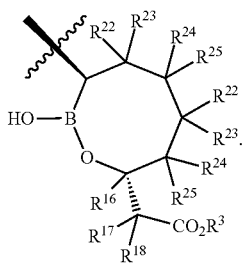

In some embodiments is a compound of Formula I, wherein $R^{22}$, $R^{23}$, $R^{24}$ and $R^{25}$ are H.

In some embodiments is a compound of Formula I, wherein X is

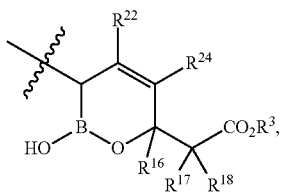

and $R^{22}$ and $R^{24}$ are independently H, Cl, F, CN, CF$_3$, —$R^{19}$, —$OR^{19}$, —C(=O)NR$^{19}$R$^{20}$, or —C(=O)OR$^{19}$. In some embodiments is a compound of Formula I, wherein X is

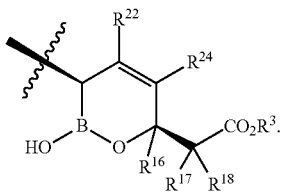

In some embodiments is a compound of Formula I, wherein X is

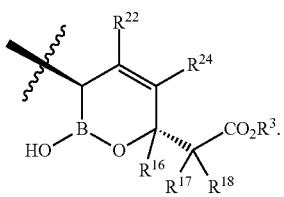

In some embodiments is a compound of Formula I, wherein $R^{22}$ and $R^{24}$ are H.

In some embodiments is a compound of Formula I, wherein X is

[Structure: 7-membered ring with B-OH, O, R^16, R^17, R^18, CO_2R^3, R^22, R^23, R^24]

and each $R^{22}$, $R^{23}$, and $R^{24}$ are independently H, Cl, F, CN, $CF_3$, $-R^{19}$, $-OR^{19}$, $-C(=O)NR^{19}R^{20}$, or $-C(=O)OR^{19}$. In some embodiments is a compound of Formula I, wherein X is

[Structure]

In some embodiments is a compound of Formula I, wherein X is

[Structure]

In some embodiments is a compound of Formula I, wherein $R^{22}$, $R^{23}$, and $R^{24}$ are H.

In some embodiments is a compound of Formula I, wherein X is

[Structure: 8-membered ring]

and each $R^{22}$, $R^{23}$, $R^{24}$, and $R^{25}$ are independently H, Cl, F, CN, $CF_3$, $-R^{19}$, $-OR^{19}$, $-C(=O)NR^{19}R^{20}$, or $-C(=O)OR^{19}$. In some embodiments is a compound of Formula I, wherein X is

[Structure]

In some embodiments is a compound of Formula I, wherein X is

[Structure]

In some embodiments is a compound of Formula I, wherein $R^{22}$, $R^{23}$, $R^{24}$, and $R^{25}$ are H.

In some embodiments is a compound of Formula I, wherein $R^{16}$, $R^{17}$, and $R^{18}$ are H.

In some embodiments is a compound of Formula I, wherein $R^d$ is hydrogen or $C_1$-$C_4$-alkyl. In some embodiments is a compound of Formula I, wherein $R^d$ is hydrogen.

In some embodiments is a compound of Formula I, wherein Z is $-C(=O)-$.

In some embodiments is a compound of Formula I, wherein n is 0. In some embodiments is a compound of Formula I, wherein n is 1, and $R^1$ and $R^2$ are hydrogen.

In some embodiments is a compound of Formula I, wherein M is a bond.

In some embodiments is a compound of Formula I, wherein m is 0.

In some embodiments is a compound of Formula I, wherein L is a bond.

In some embodiments is a compound of Formula I, wherein A is HetA. In some embodiments is a compound of Formula I, wherein HetA is selected from the group consisting of azetidine, oxetane, thietane, pyrrolidine, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, tetrahydrofuran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3, 4,7-tetrahydro-1H-1,3-diazepine, and 2,3,4,7-tetrahydro-1,3-oxazepine. In some embodiments is a compound of Formula I, wherein HetA is selected from the group consisting of piperidine, piperazine, pyrrolidine, tetrahydropyran, and tetrahydrofuran.

In some embodiments is a compound of Formula I, wherein A is CycA. In some embodiments is a compound of Formula I, wherein CycA is cyclohexyl.

In some embodiments is a compound of Formula I, wherein A is ArA. In some embodiments is a compound of Formula I, wherein ArA is phenyl. In some embodiments is a compound of Formula I, wherein ArA is pyridyl.

In some embodiments is a compound of Formula I, wherein each Y, provided Y is not attached directly to a heteroatom of HetA, is selected from the group consisting of:

fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —OR$^{10}$, —SR$^{10}$, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —S(O)$_{0,1,2}$(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —(CR$^6$R$^7$)$_v$NR$^4$(CR$^6$R$^7$)$_v$NR$^4$R$^5$, —NR$^4$(CR$^6$R$^7$)$_v$OR$^{10}$, —NR$^4$(CR$^6$R$^7$)$_v$S(O)$_{0,1,2}$R$^{10}$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —S(O)$_{0,1,2}$(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —S(O)$_{0,1,2}$(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —S(O)$_{0,1,2}$(CR$^6$R$^7$)$_v$N(R$^4$)C(=NR$^5$)NR$^4$R$^5$, —NR$^4$C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)C(=NR$^4$)NR$^5$C(=NR$^4$)NR$^4$R$^5$, —S(O)$_{0,1,2}$—(CR$^6$R$^7$)$_v$C(=NR$^4$)NR$^5$C(=NR$^4$)NR$^4$R$^5$, —NR$^4$C(=NR$^4$)NR$^4$R$^5$, —NR$^4$C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)-Heteroaryl-NR$^4$R$^5$, —N(R$^4$)-Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-_2$, —(CR$^6$R$^7$)$_v$(T)$^+$Q$^-$, and —O(CR$^6$R$^7$)$_v$NR$^4$R$^5$R$^{9+}$Q$^-$;

wherein:
T is pyridin-1-yl, pyrimidin-1-yl, or thiazol-3-yl;
Q is a pharmaceutically acceptable counterion;

each R$^6$ and R$^7$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;

or R$^6$ and R$^7$ taken together form an oxo, oxime, or an optionally substituted carbocycle or an optionally substituted heterocycle with the carbon to which they are attached;

R$^9$ is optionally substituted $C_1$-$C_6$ alkyl; and
v is 1-4;

or two Ys taken together with the carbon atoms to which they are attached form an optionally substituted carbocycle, an optionally substituted heterocycle, or a carbonyl group; or in the case where Y is attached directly to a heteroatom of HetA, Y is selected from the group consisting of:
—(CR$^6$R$^7$)$_v$NR$^4$R$^5$, —S(O)$_{1,2}$(CR$^6$R$^7$)$_v$NR$^4$R$^5$, —C(O)(CR$^6$R$^7$)$_v$NR$^4$R$^5$, —(CR$^6$R$^7$)$_w$N(R$^4$)C(O)(CR$^6$R$^7$)$_v$NR$^4$R$^5$, —(CR$^6$R$^7$)$_w$NR$^4$(CR$^6$R$^7$)$_w$NR$^4$R$^5$, —NR$^4$(CR$^6$R$^7$)$_w$OR$^{10}$, —(CR$^6$R$^7$)$_w$S(O)$_{0,1,2}$R$^{10}$, —C(O)NR$^4$(CR$^6$R$^7$)$_w$NR$^4$R$^5$, —S(O)$_{1,2}$NR$^4$(CR$^6$R$^7$)$_w$NR$^4$R$^5$, —C(=NR$^7$)NR$^4$(CR$^6$R$^7$)$_v$NR$^4$R$^5$, —C(=NR$^5$)R$^6$, —(CR$^6$R$^7$)$_w$N(R$^4$)C(=NR$^5$)R$^6$, —S(O)$_{1,2}$(CR$^6$R$^7$)$_v$N(R$^4$)C(=NR$^5$)R$^6$, —(CR$^6$R$^7$)$_v$C(=NR$^5$)NR$^4$R$^5$, —(CR$^6$R$^7$)$_w$C(=NR$^5$)NR$^4$R$^5$, —S(O)$_{1,2}$(CR$^6$R$^7$)$_v$C(=NR$^5$)NR$^4$R$^5$, —(CR$^6$R$^7$)$_w$N(R$^4$)C(=NR$^5$)NR$^4$R$^5$, —S(O)$_{1,2}$(CR$^6$R$^7$)$_v$N(R$^4$)C(=NR$^5$)NR$^4$R$^5$, —C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —S(O)$_{1,2}$—(CR$^6$R$^7$)$_v$C(=NR$^4$)NR$^5$C(=NR$^4$)NR$^4$R$^5$, —C(=NR$^4$)NR$^4$R$^5$, —C(=NR$^4$)NR$^4$C(O)R$^6$, —SO$_2$R$^6$, —C(O)R$^6$, —C(=O)OR$^6$, —C(O)NR$^4$R$^5$, —(CR$^6$R$^7$)$_v$C(O)NR$^4$R$^5$, —SO$_2$NR$^4$R$^5$, -aryl, -heteroaryl, —C(O)N(R$^4$)-Heteroaryl-NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —(CR$^6$R$^7$)$_v$NR$^5$-Heteroaryl, —(CR$^6$R$^7$)$_v$NR$^5$-Heterocyclyl, —(CR$^6$R$^7$)$_v$O-Heterocyclyl, —R$^{9+}$Q$^-$, —(CR$^6$R$^7$)$_w$NR$^4$R$^5$R$^{9+}$Q$^-$, —R$^{9+}$(CR$^6$R$^7$)$_v$NR$^4$R$^5$R$^{9+}$Q$^-_2$ and —(CR$^6$R$^7$)$_v$(T)$^+$Q;

wherein:
T is pyridin-1-yl, pyrimidin-1-yl, or thiazol-3-yl;
Q is a pharmaceutically acceptable counterion;
each R$^6$ and R$^7$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;

or $R^6$ and $R^7$ taken together form an oxo, oxime, or an optionally substituted carbocycle or an optionally substituted heterocycle with the carbon to which they are attached;

$R^9$ is optionally substituted $C_1$-$C_6$ alkyl;

v is 1-4; and w is 2-4.

In some embodiments is a compound of Formula I, wherein at least one Y is selected from the group consisting of fluoro, chloro, —CN, optionally substituted $C_1$-$C_6$ alkyl, —OH, —$OR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$C(O)NR^4(CR^6R^7)_vNR^4R^5$, —$S(O)_{0,1,2}NR^4(CR^6R^7)_vNR_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)_vNR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$(CR^6R^7)_vC(=NR^5)NR^4R^5$, —$NR^4(CR^6R^7)_vC(=NR)NR^4R^5$, —$O(CR^6R^7)_vC(=NR^5)NR^4R^5$, —$(CR^6R^7)_vN(R^4)C(=NR)NR^4R^5$, —$NR^4(CR^6R^7)_vN(R^4)C(=NR^5)NR^4R^5$, —$O(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$-Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, and —$O(CR^6R^7)_v$O-Heterocyclyl.

In some embodiments is a compound of Formula I, wherein at least one Y is selected from the group consisting of fluoro, chloro, —CN, optionally substituted $C_1$-$C_6$ alkyl, —OH, —$NR^4R^5$, —$(CR^6R^7)_vNR^4R^5$, —$NR^4(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C(=NR^7)_vNR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$(CR^6R^7)_vC(=NR^5)NR^4R^5$, —$NR^4(CR^6R^7)_vC(=NR)NR^4R^5$, —$(CR^6R^7)_vN(R^4)C(=NR^5)NR^4R^5$, —$NR^4(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)C(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4C(O)R^6$, —$(CR^6R^7)_vC(O)NR^4R^5$, -Heterocyclyl-$NR^4R^5$, -Heterocyclyl-$N(R^4)C(=NR^5)NR^4R^5$, —$N(R^4)$-Heterocyclyl-$NR^4R^5$, —$(CR^6R^7)_v$Heterocyclyl-$NR^4R^5$, —$(CR^6R^7)_v$Heterocyclyl-$N(R^4)C(=NR^5)NR^4R^5$, —$(CR^6R^7)_v$Heterocyclyl, and —$NR^4(CR^6R^7)_v$Heterocyclyl.

In some embodiments is a compound of Formula I, wherein at least one Y is selected from the group consisting of —$NR^4R^5$, —$NR^4C(=NR^5)NR^4R^5$, —$C(=NR^4)NR^4R^5$, —$N(R^4)C(=NR^5)R^6$, —$(CR^6R^7)_vNR^4R^5$, —$(CR^6R^7)_vN(R^4)C(=NR^5)NR^4R^5$, —$NR^4(CR^6R^7)_vNR^4R^5$, —$NR^4(CR^6R^7)OR^{10}$, —$(CR^6R^7)_vNR^4(CR^6R^7)_vNR^4R^5$, $NR^5C(=NR^5)NR^4(CR^6R^7)_vNR^4R^5$, —$NR^4(CR^6R^7)_vN(R^4)C(=NR^5)NR^4R^5$, —$NR^5C(O)CR^6(NR^4R^5)(CR^6R^7)_vNR^4R^5$, —$(CR^6R^7)C(=NR^5)NR^4R^5$, —$(CR^6R^7)_vN(R^4)C(O)(CR^6R^7)_vNR^4R^5$, —$C(=NR^4)NR^4C(O)R^6$, —$NR^4(CR^6R^7)_v$Heteroaryl, and —$O(CR^6R^7)_vNR^4R^5$.

In some embodiments is a compound of Formula I, wherein at least one Y is selected from the group consisting of -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$-Heterocyclyl-$NR^4R^5$, -Heteroaryl-$C(=NR)NR^4R^5$, -Heterocyclyl-$C(=NR^5)NR^4R^5$, —$(CR^6R^7)$Heteroaryl-$NR^4R^5$, —$(CR^6R^7)$Heterocyclyl-$NR^4R^5$, —$(CR^6R^7)_v$Heteroaryl-$N(R^4)C(=NR^5)NR^4R^5$, and —$(CR^6R^7)$Heterocyclyl-$N(R^4)C(=NR^5)NR^4R^5$.

In some embodiments is a compound of Formula I, wherein at least one Y is 2-($NR^4R^5$)-pyridyl, 2-($NR^4R^5$)-pyrimidinyl, 2-($NR^4R^5$)-thiazolyl, 2-($NR^4R^5$)-imidazolyl, 3-($NR^4R^5$)-pyrazolyl, 3-($NR^4R^5$)-isothiazolyl, 2-($NR^4R^5$)-oxazolyl, piperidine, pyrrolidine, 4-amino-piperidinyl, 3-amino-pyrrolidinyl, piperazine, or 4-carboximidoyl-piperazinyl.

In some embodiments is a compound of Formula I, wherein two Y groups, together with the atoms to which they are attached form a pyrrolidine ring.

In some embodiments is a compound of Formula I, wherein p is 1 or 2.

In some embodiments is a compound of Formula I, wherein $R^4$ and $R^5$ are independently selected from the group consisting of hydrogen, optionally substituted $C_1$-$C_6$ alkyl, optionally substituted alkoxyalkyl, optionally substituted hydroxyalkyl, and optionally substituted heterocyclyl. In some embodiments is a compound of Formula I, wherein $R^4$ and $R^5$ are independently hydrogen or optionally substituted $C_1$-$C_6$ alkyl.

In some embodiments is a compound of Formula I, wherein $R^6$ and $R^7$ are independently selected from the group consisting of hydrogen, halogen, optionally substituted $C_1$-$C_6$ alkyl, —OH, —$NR^4R^5$, and optionally substituted heterocyclyl, or $R^6$ and $R^7$ taken together form an optionally substituted heterocycle with the carbon to which they are attached. In some embodiments some embodiments is a compound of Formula I, wherein $R^6$ and $R^7$ are independently hydrogen, fluoro, or optionally substituted $C_1$-$C_6$ alkyl.

In some embodiments is a compound of Formula I, wherein $R^3$ is H.

In some embodiments is a compound of Formula I, wherein $R^3$ is $R^{31}$. In some embodiments is a compound of Formula I, wherein $R^3$ is $C_1$-$C_{12}$ alkyl. In some embodiments is a compound of Formula I, wherein $R^3$ is methyl, ethyl, propyl, butyl, or isopropyl.

In some embodiments is a compound of Formula I, wherein $R^3$ is selected from the group consisting optionally substituted $C_1$-$C_{12}$ alkenyl, optionally substituted $C_1$-$C_{12}$ alkynyl, $C_3$-$C_8$ cycloalkyl, $C_3$-$C_8$ heterocycloalkyl, optionally substituted aryl, optionally substituted heteroaryl, optionally substituted alkylcycloalkyl, optionally substituted alkylheterocycloalkyl, optionally substituted alkylaryl, and optionally substituted alkylheteroaryl.

In some embodiments is a compound of Formula I, wherein $R^3$ is optionally substituted $C_1$-$C_{12}$ alkyl, alkyloxyalkyl, acyloxyalkyl, alkyloxycarbonyloxyalkyl, cycloalkyloxycarbonyloxyalkyl, aryloxycarbonyloxyalkyl, or alkyl-[1,3]dioxol-2-one. In some embodiments is a compound of Formula I, wherein $R^3$ is acyloxyalkyl. In some embodiments is a compound of Formula I, wherein $R^3$ is —$CH_2OC(=O)CH_3$ or —$CH_2OC(=O)C(CH_3)_3$.

In some embodiments is a compound of Formula I, wherein $R^3$ is —$(R^{30})_qOR^{31}$ or —$(R^{30})_qO(R^{30})_qOR^{31}$.

In some embodiments is a compound of Formula I, wherein $R^3$ is selected from the group consisting of —$R^{30}OC(O)R^{31}$, —$R^{30}OC(O)OR^{31}$, —$R^{30}OC(O)NHR^{31}$, and —$R^{30}OC(O)N(R^{31})_2$.

In some embodiments is a compound of Formula I, wherein $R^3$ is selected from the group consisting of:

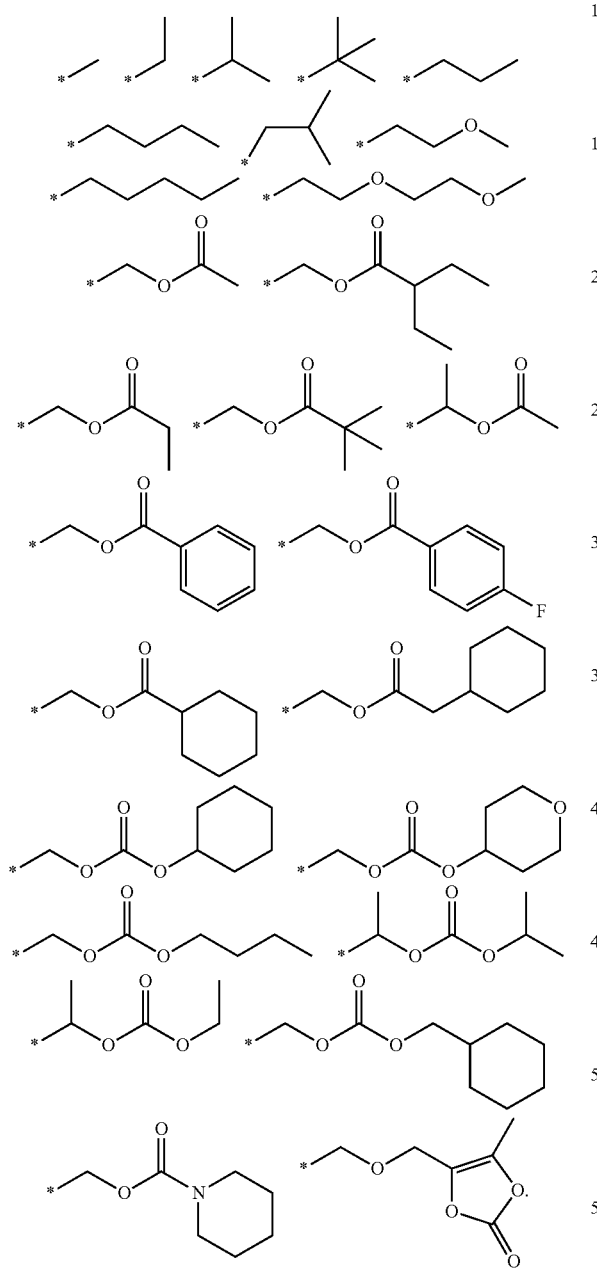

In some embodiments is a compound of Formula I, wherein $R^3$ is selected from the group consisting of methyl, ethyl, butyl, pivaloyloxymethyl, acetoxymethyl, ethoxycarbonyloxymethyl, 1-(acetoxy)ethyl, 1-(pivaloyloxy)ethyl, 1-(isopropoxycarbonyoxy)ethyl, and 1-cyclohexyloxycarbonyloxymethyl.

In certain embodiments of a compound of Formula I, the compound is selected from the group represented by the following structures:

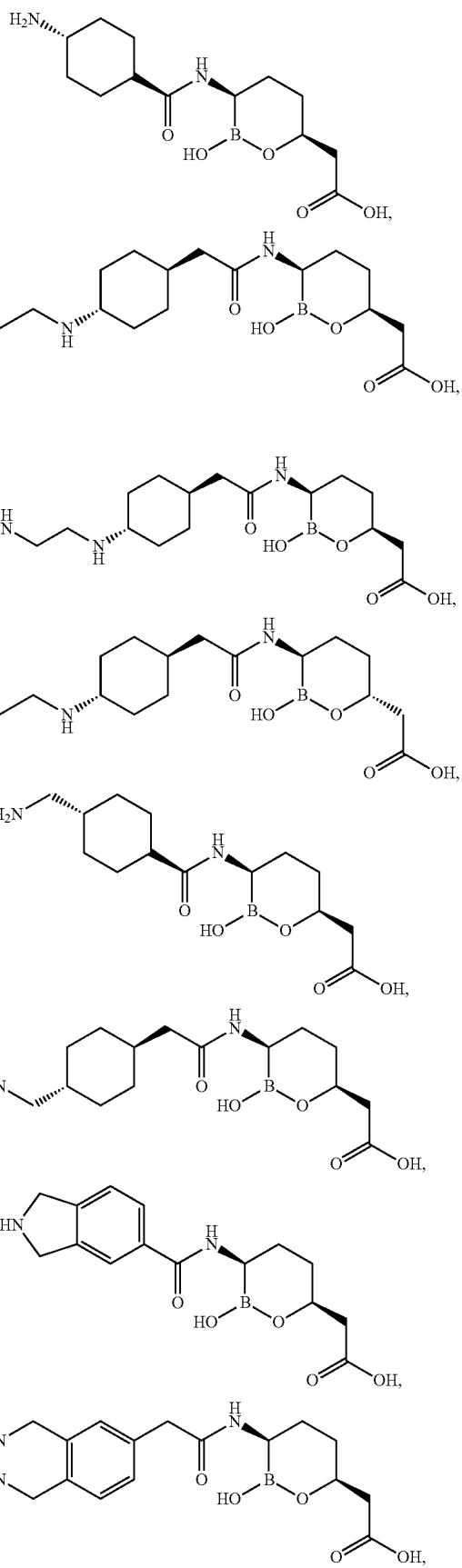

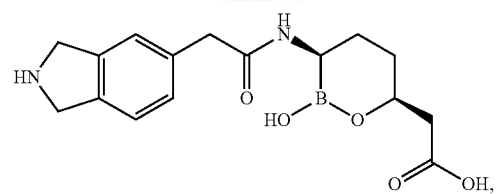
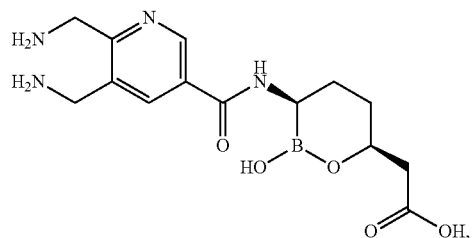
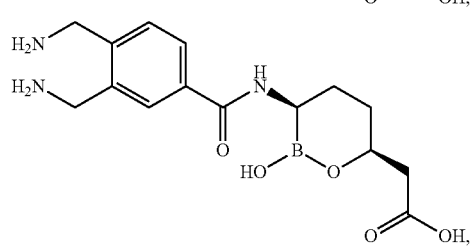
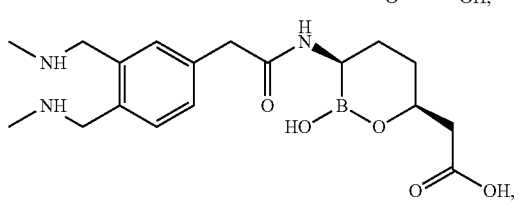
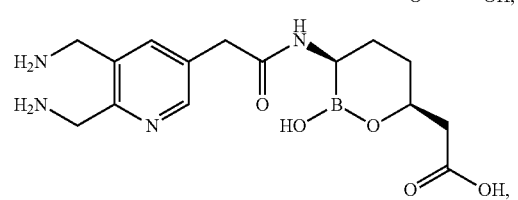
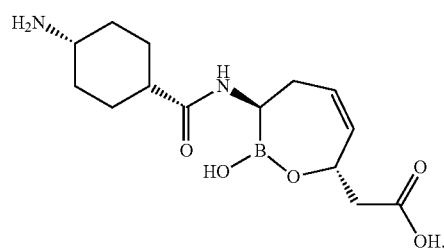
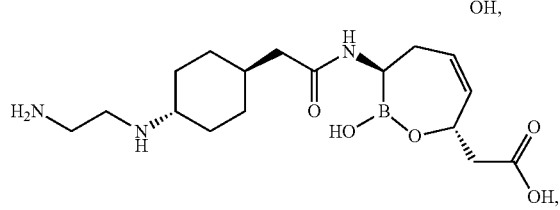
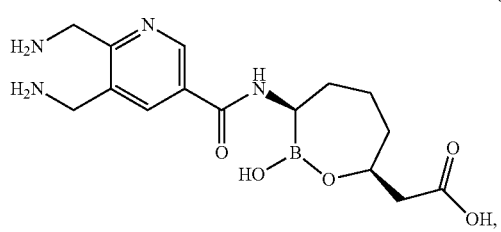
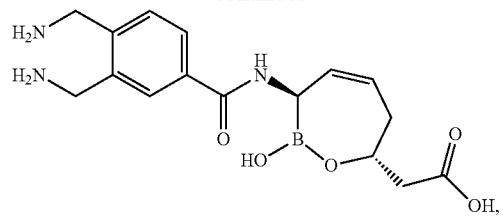
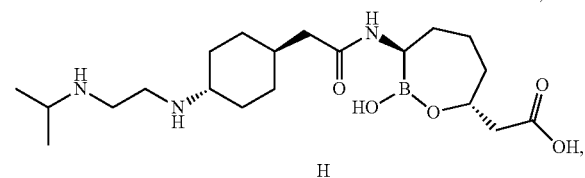
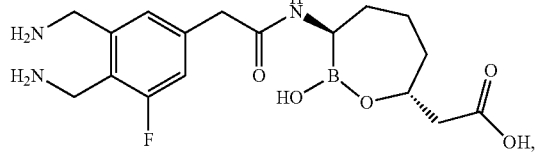
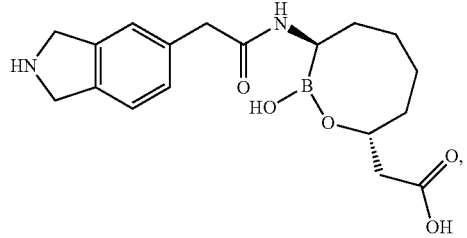
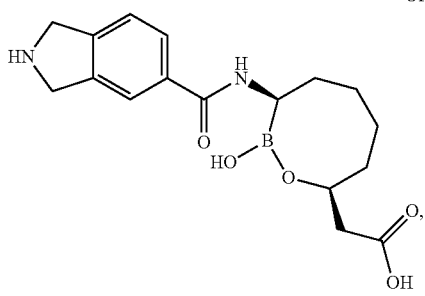
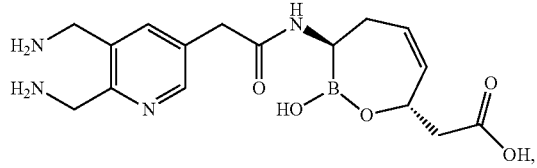
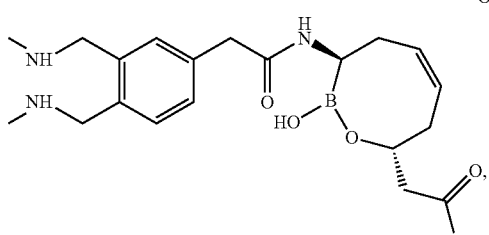
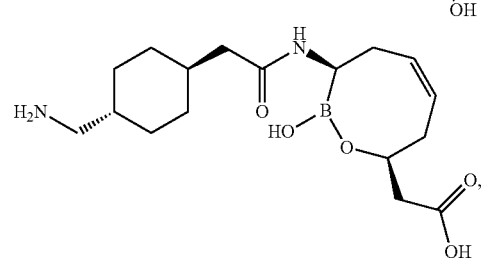

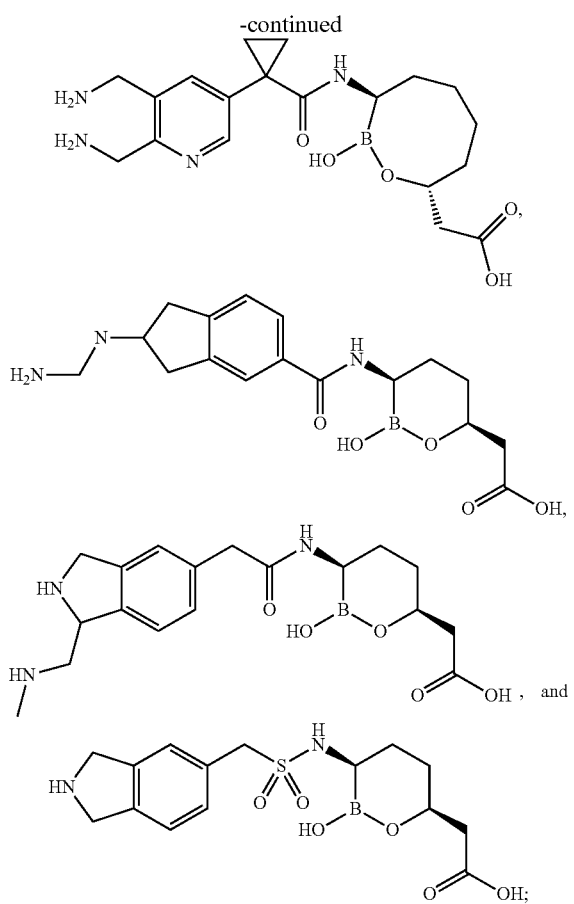

or a pharmaceutically acceptable salt, N-oxide, or isomer thereof.

In another aspect, provided herein, is a pharmaceutical composition comprising a compound of Formula I or a pharmaceutically acceptable salt, N-oxide, or isomer thereof, and a pharmaceutically acceptable excipient. In some embodiments is a pharmaceutical composition of Formula I, further comprising a beta-lactam antibiotic. In some embodiments is a pharmaceutical composition of Formula I, further comprising a beta-lactam antibiotic wherein the beta-lactam antibiotic is a penicillin, cephalosporin, carbapenem, monobactam, bridged monobactam, or a combination thereof.

In some embodiments, the compound of Formula I is the stereoisomer represented by any of the structures shown herein. In some embodiments, the compound of Formula I is an enantiomer of the stereoisomer represented by any of the structures shown herein. In certain embodiments, the compound of Formula I is a diastereomer of the stereoisomer represented by any of the structures shown herein. In some embodiments, the compound of Formula I is a mixture of enantiomers and/or diastereomers of the stereoisomer represented by any of the structures shown herein. In certain embodiments, the compound of Formula I is a racemate of the stereoisomer represented by any of the structures herein.

In a further aspect, provided herein are methods of treating a bacterial infection in a subject, comprising administering to the subject a compound of Formula I as described herein, optionally in combination with a beta-lactam antibiotic. In some embodiments, provided herein, are methods of treating a bacterial infection in a subject, comprising administering to the subject a compound of Formula I as described herein. In some embodiments, provided herein, are methods of treating a bacterial infection in a subject, comprising administering to the subject a compound of Formula I as described herein in combination with a therapeutically effective amount of beta-lactam antibiotic. In some embodiments, provided herein, are methods of treating a bacterial infection in a subject, comprising administering to the subject a compound of Formula I as described herein in combination with a therapeutically effective amount of beta-lactam antibiotic wherein the beta-lactam antibiotic is a penicillin, cephalosporin, carbapenem, monobactam, bridged monobactam, or a combination thereof.

In a further aspect, provided herein are methods of treating a bacterial infection in a subject, comprising administering to the subject a pharmaceutical composition as described herein, optionally in combination with a beta-lactam antibiotic. In some embodiments, provided herein are methods of treating a bacterial infection in a subject, comprising administering to the subject a pharmaceutical composition as described herein. In some embodiments, the methods of treating a bacterial infection in a subject comprise administering to the subject a pharmaceutical composition as described herein in combination with a beta-lactam antibiotic. In some embodiments, the methods of treating a bacterial infection in a subject comprise administering to the subject a pharmaceutical composition as described herein in combination with a beta-lactam antibiotic wherein the beta-lactam antibiotic is a penicillin, cephalosporin, carbapenem, monobactam, bridged monobactam, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases—for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases—as well as Class B metallo-beta-lactamases (e.g. VIM, NDM) has begun to diminish the utility of the beta-lactam antibiotic family, including the more recent generation beta-lactam drugs, leading to a serious medical problem. Indeed the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These beta-lactamase inhibitors are poorly active against the diversity of beta-lactamse enzymes (both serine- and metallo-based) now emerging clinically. In addition, these enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta-lactamase inhibitors are largely ineffective against the new Class A and Class B carbapenemases, against the chromosomal and plasmid-mediated Class C cephalosporinases and against many of the Class D oxacillinases.

To address this growing therapeutic vulnerability, and because there are three major molecular classes of serine-based beta-lactamases, and one major class of metallo-beta-lactamases, and each of these classes contains significant numbers of beta-lactamase variants, we have identified an approach for developing novel beta-lactamase inhibitors with broad spectrum functionality. In particular, we have identified an approach for developing compounds that are active against both serine- and metallo-based beta-lactamase enzymes. Compounds of the current invention demonstrate potent activity across all four major classes of beta-lactamases.

The present invention is directed to certain boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase. β-Lactamases of interest include those disclosed in an ongoing website that monitors beta-lactamase nomenclature (www.lahey.org) and in Bush, K. and G. A. Jacoby. 2010. An updated functional classification of β-lactamases. Antimicrob. Agents Chemother. 54:969-976. β-Lactamases of particular interest herein include β-lactamases found in bacteria such as class A β-lactamases including the SHV, CTX-M and KPC subclasses, class B β-lactamases such as VIM, class C β-lactamases (both chromosomal and plasmid-mediated), and class D β-lactamases. The term "β-lactamase inhibitor" refers to a compound which is capable of inhibiting β-lactamase activity. Inhibiting β-lactamase activity means inhibiting the activity of a class A, B, C, or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in Bush, K. and G. A. Jacoby. 2010. An updated functional classification of β-lactamases. Antimicrob. Agents Chemother. 54:969-976.

The terms below, as used herein, have the following meanings, unless indicated otherwise:

"Amino" refers to the —NH$_2$ radical.

"Cyano" or "nitrile" refers to the —CN radical.

"Hydroxy" or "hydroxyl" refers to the —OH radical.

"Nitro" refers to the —NO$_2$ radical.

"Oxo" refers to the =O substituent.

"Oxime" refers to the =N—OH substituent.

"Thioxo" refers to the =S substituent.

"Alkyl" refers to an optionally substituted straight-chain, or optionally substituted branched-chain saturated hydrocarbon monoradical having from one to about ten carbon atoms, more preferably one to six carbon atoms, wherein an sp3-hybridized carbon of the alkyl residue is attached to the rest of the molecule by a single bond. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1- pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. Unless stated otherwise specifically in the specification, an alkyl group may be optionally substituted as described below, for example, with oxo, amino, nitrile, nitro, hydroxyl, alkyl, alkylene, alkynyl, alkoxy, aryl, cycloalkyl, heterocyclyl, heteroaryl, and the like.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

"Alkylene" or "alkylene chain" refers to a straight or branched divalent hydrocarbon chain. Unless stated otherwise specifically in the specification, an alkylene group may be optionally substituted as described below.

"Alkoxy" or "alkyloxy" refers to a radical of the formula —$OR_a$ where $R_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocyclyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0] octane, bicyclo[4.3.0]nonane, cis-decalin, trans-decalin, bicyclo[2.1.1]hexane, bicyclo[2.2.1]heptane, bicyclo[2.2.2] octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

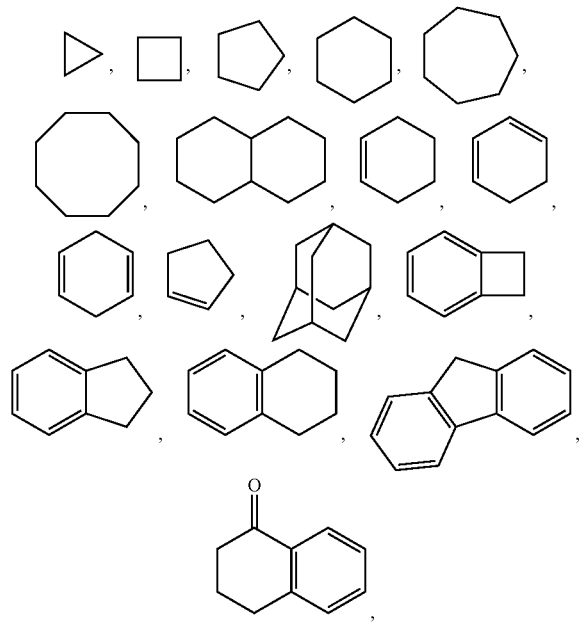

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

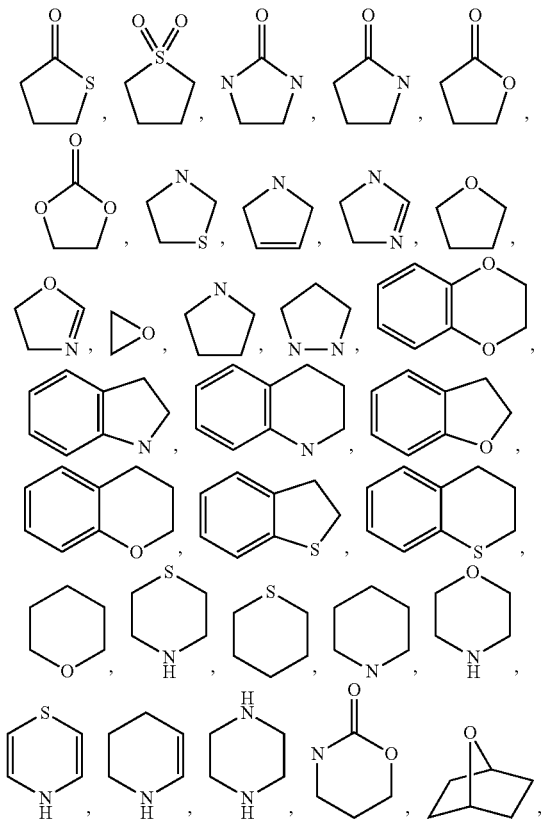

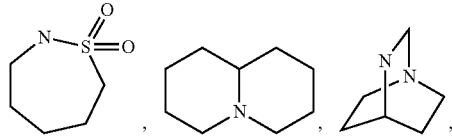

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

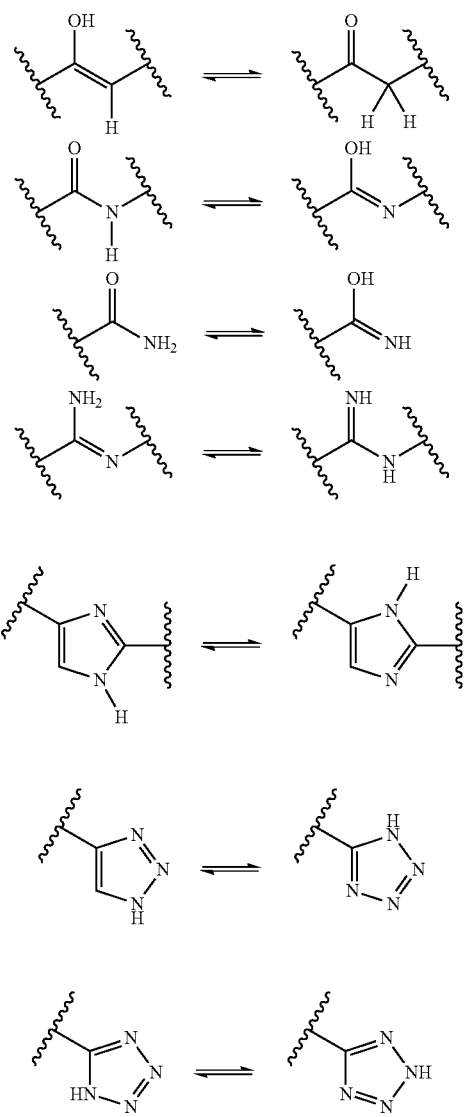

Compounds

Described herein are compounds that modulate the activity of beta-lactamase. In some embodiments, the compounds described herein inhibit beta-lactamase. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula I or pharmaceutically acceptable salts, tautomers, or N-oxides thereof:

Formula (I)

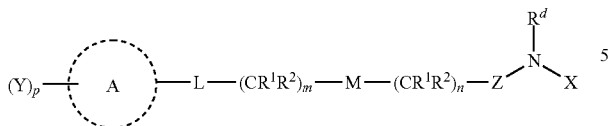

wherein:

L is a bond, —C(R$^1$R$^2$)—, —C(=O)—, or =C(R$^1$)—;

M is a bond, —O—, —S—, —S(O)—, —S(O)$_2$—, or —N(R$^4$)—;

m is 0, 1, or 2;

n is 0, 1, 2, or 3;

p is 0, 1, 2, 3, or 4;

Z is —C(=O)—, —C(=S), or —S(O)$_2$—;

A is CycA, ArA or HetA, wherein

CycA is an optionally substituted 3-10 membered non-aromatic carbocycle, wherein an optional olefin functionality of the non-aromatic carbocycle is not directly attached to an oxygen, sulfur, or nitrogen substituent;

ArA is an aromatic or heteroaromatic ring system optionally substituted with one or more substituents selected from the group consisting of fluoro, chloro, bromo, —CN, optionally substituted C$_1$-C$_6$ alkyl, optionally substituted C$_3$-C$_6$ cycloalkyl, optionally substituted heterocycle, optionally substituted aryl, optionally substituted heteroaryl, —OH, —OR$^{10}$, and —SR$^{10}$;

HetA is an optionally substituted non-aromatic heterocyclic ring system;

each R$^1$ and R$^2$ is independently selected from the group consisting of hydrogen, fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$, or R$^1$ and R$^2$ taken together form an oxo, oxime, or an optionally substituted carbocycle or optionally substituted heterocycle with the carbon to which they are attached;

each R$^d$, R$^4$, and R$^5$ is independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^4$ and R$^5$ taken together form an optionally substituted heterocycle with the nitrogen to which they are attached;

each R$^{10}$ is independently selected from the group consisting of optionally substituted C$_1$-C$_6$ alkyl and optionally substituted C$_3$-C$_6$ cycloalkyl;

each Y is independently a group comprising 1-50 non-hydrogen atoms selected from the group consisting of C, N, O, S, and P; and X is

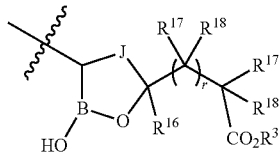

J is a 1-4 atom alkylene or 1-4 atom alkenylene, optionally substituted by one or more substituents selected from the group consisting of Cl, F, CN, CF$_3$, —R$^{19}$, —OR$^{19}$, —C(=O)NR$^{19}$R$^{20}$, and —C(=O)OR$^{19}$, wherein said 1-4 atom alkylene or 1-4 atom alkenylene is optionally fused to an optionally substituted aryl, optionally substituted heteroaryl, optionally substituted carbocyclyl, or optionally substituted heterocyclyl;

R$^3$ is selected from the group consisting of R$^{31}$, —(R$^{30}$)$_q$OR$^{31}$, —(R$^{30}$)$_q$O(R$^{30}$)$_q$OR$^{31}$, —R$^{30}$OC(O)R$^{31}$, —R$^{30}$OC(O)OR$^{31}$, —R$^{30}$OC(O)NHR$^{31}$, —R$^{30}$OC(O)N(R$^{31}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one;

each R$^{30}$ is independently —CH$_2$—, —CH(CH$_3$)—, —C(CH$_3$)$_2$—, or optionally substituted 1,1'-cyclopropylene;

R$^{31}$ is selected from the group consisting of optionally substituted C$_1$-C$_{12}$ alkyl, optionally substituted C$_1$-C$_{12}$ alkenyl, optionally substituted C$_1$-C$_{12}$ alkynyl, C$_3$-C$_8$ cycloalkyl, C$_3$-C$_8$ heterocycloalkyl, optionally substituted aryl, optionally substituted heteroaryl, optionally substituted alkylcycloalkyl, optionally substituted alkylheterocycloalkyl, optionally substituted alkylaryl, and optionally substituted alkylheteroaryl;

each q is independently 2, 3, 4, 5, or 6;

R$^{16}$ is selected from a group consisting of H, —C$_1$-C$_9$alkyl, —C$_2$-C$_9$alkenyl, —C$_2$-C$_9$alkynyl, carbocyclyl, —C$_1$-C$_9$alkylR$^{21}$, —C$_2$-C$_9$alkenylR$^{21}$, —C$_2$-C$_9$alkynylR$^{21}$, carbocyclylR$^{21}$, —C(=O)OR$^{19}$, —C$_1$-C$_9$alkylC(=O)OR$^{19}$, —C$_2$-C$_9$alkenylC(=O)OR$^{19}$, —C$_2$-C$_9$alkynylC(=O)OR$^{19}$, carbocyclylC(=O)OR$^{19}$, or alternatively:

(i) R$^{16}$ and an R$^{17}$ are taken together with the atoms to which they are attached to form a substituted or unsubstituted carbocyclyl or substituted or unsubstituted heterocyclyl, (ii) R$^{16}$ and a carbon atom in J are taken together with intervening atoms to form a substituted or unsubstituted carbocyclyl or substituted or unsubstituted heterocyclyl, or (iii) R$^{16}$ is absent when the carbon to which it is attached is a ring atom in an aryl or heteroaryl ring;

each R$^{17}$ is independently selected from a group consisting of H, halo, —C$_1$-C$_9$alkyl, —C$_2$-C$_9$alkenyl, —C$_2$-C$_9$alkynyl, NR$^{19}$R$^{20}$, —OR$^{19}$, —C$_1$-C$_9$alkylC(=O)OR$^{19}$, —C$_2$-C$_9$alkenylC(=O)OR$^{19}$, —C$_2$-C$_9$alkynylC(=O)OR$^{19}$, carbocyclylC(=O)OR$^{19}$, or independently:

(i) R$^{16}$ and an R$^{17}$ are taken together with the atoms to which they are attached to form a substituted or unsubstituted carbocyclyl or substituted or unsubstituted heterocyclyl, (ii) $R^{17}$ and an $R^{18}$ are taken together with the atoms to which they are attached to form a substituted or unsubstituted carbocyclyl or substituted or unsubstituted heterocyclyl, (iii) an $R^{17}$ and a carbon atom in J are taken together with intervening atoms to form a substituted or unsubstituted carbocyclyl or substituted or unsubstituted heterocyclyl;

each $R^{18}$ is independently selected from a group consisting of H, halo, —$C_2$-$C_9$alkenyl, —$C_2$-$C_9$alkynyl, $NR^{19}R^{20}$, —$OR^{19}$, —$C_1$-$C_9$alkylC(=O)$OR^{19}$, —$C_2$-$C_9$alkenylC(=O)$OR^{19}$, —$C_2$-$C_9$alkynylC(=O)$OR^{19}$, carbocyclylC(=O)$OR^{19}$, or independently:

(i) an $R^{17}$ and an $R^{18}$ are taken together with the atoms to which they are attached to form a substituted or unsubstituted carbocyclyl or substituted or unsubstituted heterocyclyl, (ii) a geminal $R^{17}$ and $R^{18}$ together form —$C_2$-$C_9$alkenylC(=O)$OR^{19}$, or (iii) each $R^{18}$ attached to a ring atom forming part of a substituted or unsubstituted aryl is absent;

each $R^{19}$ is independently selected from a group consisting of H, —$C_1$-$C_9$alkyl, —$C_2$-$C_9$alkenyl, —$C_2$-$C_9$alkynyl, carbocyclyl, —$C_1$-$C_9$alkyl$R^{21}$, —$C_2$-$C_9$alkenyl$R^{21}$, —$C_2$-$C_9$alkynyl$R^{21}$, carbocyclyl$R^{21}$, substituted or unsubstituted aryl, substituted or unsubstituted heteroaryl, substituted or unsubstituted carbocyclyl, and substituted or unsubstituted heterocyclyl;

each $R^{20}$ is independently selected from a group consisting of H, —$C_1$-$C_9$alkyl, —$OR^{19}$, —CH(=NH), —C(=O)$OR^{19}$, substituted or unsubstituted aryl, substituted or unsubstituted heteroaryl, substituted or unsubstituted carbocyclyl, and substituted or unsubstituted heterocyclyl;

each $R^{21}$ is independently selected from a group consisting of substituted or unsubstituted aryl, substituted or unsubstituted heteroaryl, substituted or unsubstituted carbocyclyl, and substituted or unsubstituted heterocyclyl; and r is 0 or 1, wherein each —$C_1$-$C_9$alkyl, —$C_2$-$C_9$alkenyl, and —$C_2$-$C_9$alkynyl is independently optionally substituted.

In some embodiments is a compound of Formula I, wherein X is

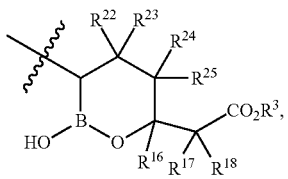

and $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$. In some embodiments is a compound of Formula I, wherein X is

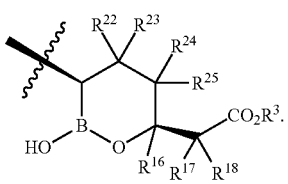

In some embodiments is a compound of Formula I, wherein X is

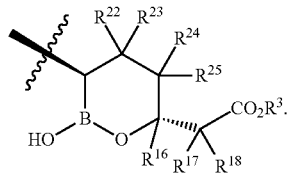

In some embodiments is a compound of Formula I, wherein $R^{22}$, $R^{23}$, $R^{24}$, and $R^{25}$ are H.

In some embodiments is a compound of Formula I, wherein X is

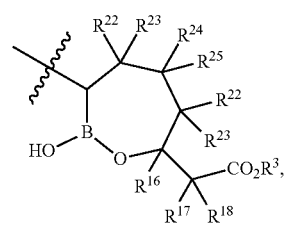

and each $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$. In some embodiments is a compound of Formula I, wherein X is

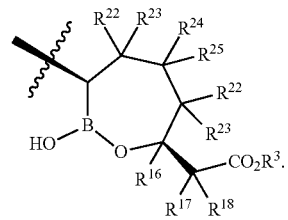

In some embodiments is a compound of Formula I, wherein X is

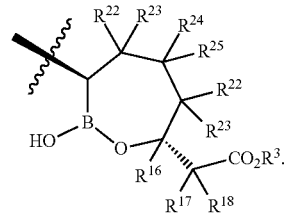

In some embodiments is a compound of Formula I, wherein $R^{22}$, $R^{23}$, $R^{24}$, and $R^{25}$ are H.

In some embodiments is a compound of Formula I, wherein X is

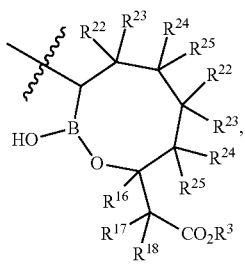

and each $R^{22}$, $R^{23}$, $R^{24}$, and $R^{25}$ are independently H, Cl, F, CN, $CF_3$, $-R^{19}$, $-OR^{19}$, $-C(=O)NR^{19}R^{20}$, or $-C(=O)OR^{19}$. In some embodiments is a compound of Formula I, wherein X is

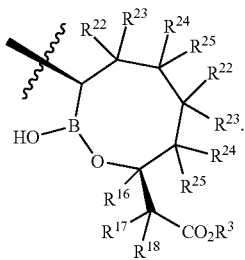

In some embodiments is a compound of Formula I, wherein X is

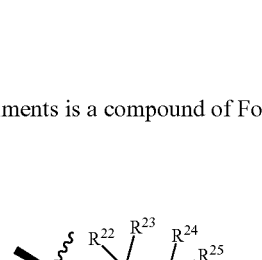

In some embodiments is a compound of Formula I, wherein $R^{22}$, $R^{23}$, $R^{24}$, and $R^{25}$ are H.

In some embodiments is a compound of Formula I, wherein X is

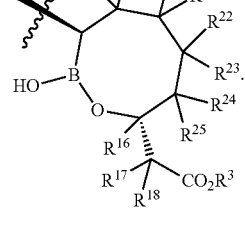

and $R^{22}$ and $R^{24}$ are independently H, Cl, F, CN, $CF_3$, $-R^{19}$, $-OR^{19}$, $-C(=O)NR^{19}R^{20}$, or $-C(=O)OR^{19}$. In some embodiments is a compound of Formula I, wherein X is

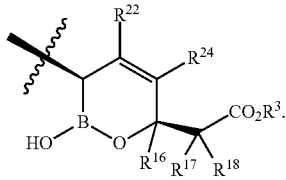

In some embodiments is a compound of Formula I, wherein X is

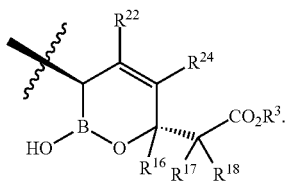

In some embodiments is a compound of Formula I, wherein $R^{22}$ and $R^{24}$ are H.

In some embodiments is a compound of Formula I, wherein X is

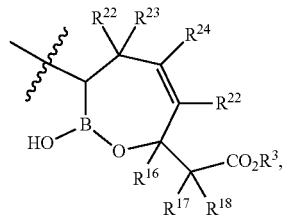

and each $R^{22}$, $R^{23}$, and $R^{24}$ are independently H, Cl, F, CN, $CF_3$, $-R^{19}$, $-OR^{19}$, $-C(=O)NR^{19}R^{20}$, or $-C(=O)OR^{19}$. In some embodiments is a compound of Formula I, wherein X is

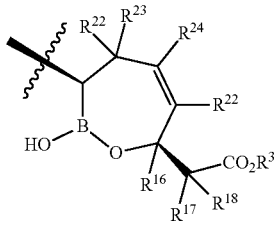

In some embodiments is a compound of Formula I, wherein X is

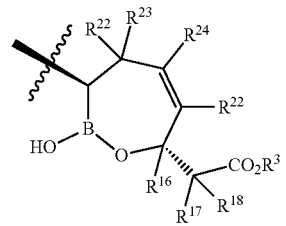

In some embodiments is a compound of Formula I, wherein $R^{22}$, $R^{23}$, and $R^{24}$ are H.

In some embodiments is a compound of Formula I, wherein X is

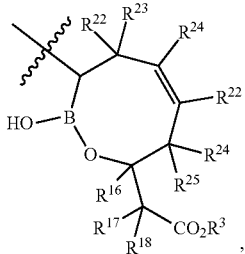

and each $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$. In some embodiments is a compound of Formula I, wherein X is

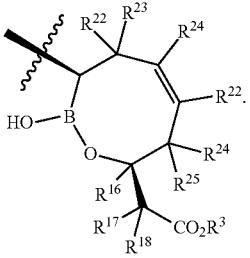

In some embodiments is a compound of Formula I, wherein X is

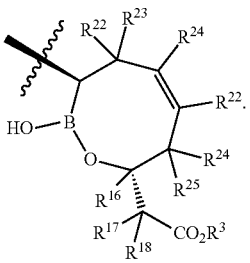

In some embodiments is a compound of Formula I, wherein $R^{22}$, $R^{23}$, $R^{24}$, and $R^{25}$ are H.

In some embodiments is a compound of Formula I, wherein $R^{16}$, $R^{17}$, and $R^{18}$ are H.

In some embodiments is a compound of Formula I, wherein $R^d$ is hydrogen or $C_1$-$C_4$-alkyl. In some embodiments is a compound of Formula I, wherein $R^d$ is hydrogen.

In some embodiments is a compound of Formula I, wherein Z is —C(=O)—.

In some embodiments is a compound of Formula I, wherein n is 0. In some embodiments is a compound of Formula I, wherein n is 1, and $R^1$ and $R^2$ are hydrogen.

In some embodiments is a compound of Formula I, wherein M is a bond.

In some embodiments is a compound of Formula I, wherein m is 0.

In some embodiments is a compound of Formula I, wherein L is a bond.

In some embodiments is a compound of Formula I, wherein A is HetA. In some embodiments is a compound of Formula I, wherein HetA is selected from the group consisting of azetidine, oxetane, thietane, pyrrolidine, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, tetrahydrofuran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-1H-1,3-diazepine, and 2,3,4,7-tetrahydro-1,3-oxazepine. In some embodiments is a compound of Formula I, wherein HetA is selected from the group consisting of piperidine, piperazine, pyrrolidine, tetrahydropyran, and tetrahydrofuran.

In some embodiments is a compound of Formula I, wherein A is CycA. In some embodiments is a compound of Formula I, wherein CycA is cyclohexyl.

In some embodiments is a compound of Formula I, wherein A is ArA. In some embodiments is a compound of Formula I, wherein ArA is phenyl. In some embodiments is a compound of Formula I, wherein ArA is pyridyl.

In some embodiments is a compound of Formula I, wherein each Y, provided Y is not attached directly to a heteroatom of HetA, is selected from the group consisting of:

fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, —$SR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$S(O)_{0,1,2}(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$S(O)_{0,1,2}(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$S(O)_{0,1,2}(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$S(O)_{0,1,2}—(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, —SO$_2$NR$^4$R$^5$, -Heteroaryl-NR$^4$R$^5$, -Heterocyclyl-NR$^4$R$^5$, -Heteroaryl-N(R$^4$)C(═NR$^5$)NR$^4$R$^5$, -Heterocyclyl-N(R$^4$)C(═NR$^5$)NR$^4$R$^5$, —N(R$^4$)-Heteroaryl-NR$^4$R$^5$, —N(R$^4$)-Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(═NR$^5$)NR$^4$R$^5$, —(CR$^6$R$^7$)$_v$Heterocyclyl-N(R$^4$)C(═NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-_2$, —(CR$^6$R$^7$)$_v$(T)+Q$^-$, and —O(CR$^6$R$^7$)$_v$NR$^4$R$^5$R$^{9+}$Q$^-$;

wherein:
T is pyridin-1-yl, pyrimidin-1-yl, or thiazol-3-yl;
Q is a pharmaceutically acceptable counterion;
each R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^1$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;
or R$^6$ and R$^7$ taken together form an oxo, oxime, or an optionally substituted carbocycle or an optionally substituted heterocycle with the carbon to which they are attached;
R$^9$ is optionally substituted C$_1$-C$_6$ alkyl; and
v is 1-4;
or two Ys taken together with the carbon atoms to which they are attached form an optionally substituted carbocycle, an optionally substituted heterocycle, or a carbonyl group; or in the case where Y is attached directly to a heteroatom of HetA, Y is selected from the group consisting of:
—(CR$^6$R$^7$)$_v$NR$^4$R$^5$, —S(O)$_{1,2}$(CR$^6$R$^7$)$_v$NR$^4$R$^5$, —C(O)(CR$^6$R$^7$)$_v$NR$^4$R$^5$, —(CR$^6$R$^7$)$_w$N(R$^4$)C(O)(CR$^6$R$^7$)$_v$NR$^4$R$^5$, —(CR$^6$R$^7$)$_w$NR$^4$(CR$^6$R$^7$)$_w$NR$^4$R$^5$, —NR$^4$(CR$^6$R$^7$)$_w$OR$^{10}$, —(CR$^6$R$^7$)$_w$S(O)$_{0,1,2}$R$^{10}$, —C(O)NR$^4$(CR$^6$R$^7$)$_w$NR$^4$R$^5$, —S(O)$_{1,2}$NR$^4$(CR$^6$R$^7$)$_w$NR$^4$R$^5$, —C(═NR$^7$)NR$^4$(CR$^6$R$^7$)$_v$NR$^4$R$^5$, —C(═NR$^5$)R$^6$, —(CR$^6$R$^7$)$_w$N(R$^4$)C(═NR$^5$)R$^6$, —S(O)$_{1,2}$(CR$^6$R$^7$)$_v$N(R$^4$)C(═NR$^5$)R$^6$, —(CR$^6$R$^7$)$_v$C(═NR$^5$)NR$^4$R$^5$, —(CR$^6$R$^7$)$_w$C(═NR$^5$)NR$^4$R$^5$, —S(O)$_{1,2}$(CR$^6$R$^7$)$_v$C(═NR$^5$)NR$^4$R$^5$, —(CR$^6$R$^7$)$_w$N(R$^4$)C(═NR$^5$)NR$^4$R$^5$, —S(O)$_{1,2}$(CR$^6$R$^7$)$_v$N(R$^4$)C(═NR$^5$)NR$^4$R$^5$, —C(═NR$^5$)NR$^4$C(═NR$^5$)NR$^4$R$^5$, —(CR$^6$R$^7$)$_v$C(═NR$^4$)NR$^5$C(═NR$^4$)NR$^4$R$^5$, —S(O)$_{1,2}$—(CR$^6$R$^7$)$_v$C(═NR$^4$)NR$^5$C(═NR$^4$)NR$^4$R$^5$, —C(═NR$^4$)NR$^4$R$^5$, —C(═NR$^4$)NR$^4$C(O)R$^6$, —SO$_2$R$^6$, —C(O)R$^6$, —C(═O)OR$^6$, —C(O)NR$^4$R$^5$, —(CR$^6$R$^7$)$_v$C(O)NR$^4$R$^5$, —SO$_2$NR$^4$R$^5$, -aryl, -heteroaryl, —C(O)N(R$^4$)-Heteroaryl-NR$^4$R$^5$, -Heteroaryl-NR$^4$R$^5$, -Heterocyclyl-NR$^4$R$^5$, -Heteroaryl-N(R$^4$)C(═NR$^5$)NR$^4$R$^5$, -Heterocyclyl-N(R$^4$)C(═NR$^5$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(═NR$^5$)NR$^4$R$^5$, —(CR$^6$R$^7$)$_v$Hetero-cyclyl-N(R$^4$)C(═NR$^5$)NR$^4$R$^5$, —(CR$^6$R$^7$)$_v$Heteroaryl, —(CR$^6$R$^7$)$_v$Heterocyclyl, —(CR$^6$R$^7$)$_v$NR$^5$-Heteroaryl, —(CR$^6$R$^7$)$_v$NR$^5$-Heterocyclyl, —(CR$^6$R$^7$)$_v$O-Heterocyclyl, —R$^{9+}$Q$^-$, —(CR$^6$R$^7$)$_w$NR$^4$R$^5$R$^{9+}$Q$^-$, —R$^{9+}$(CR$^6$R$^7$)$_v$NR$^4$R$^5$R$^{9+}$Q$^-_2$ and —(CR$^6$R$^7$)$_v$(T)+Q;

wherein:
T is pyridin-1-yl, pyrimidin-1-yl, or thiazol-3-yl;
Q is a pharmaceutically acceptable counterion;
each R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;
or R$^6$ and R$^7$ taken together form an oxo, oxime, or an optionally substituted carbocycle or an optionally substituted heterocycle with the carbon to which they are attached;
R$^9$ is optionally substituted C$_1$-C$_6$ alkyl;
v is 1-4; and
w is 2-4.

In some embodiments is a compound of Formula I, wherein at least one Y is selected from the group consisting of fluoro, chloro, —CN, optionally substituted C$_1$-C$_6$ alkyl, —OH, —OR$^{10}$, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(═NR$^7$)NR$^4$(CR$^6$R$^7$)$_v$NR$^4$R$^5$, —N(R$^4$)C(═NR$^5$)R$^6$, —(CR$^6$R$^7$)$_v$N(R$^4$)C(═NR$^5$)R$^6$, —NR$^4$(CR$^6$R$^7$)$_v$N(R$^4$)C(═NR$^5$)R$^6$, —O(CR$^6$R$^7$)$_v$N(R$^4$)C(═NR$^5$)R$^6$, —(CR$^6$R$^7$)$_v$C(═NR$^5$)NR$^4$R$^5$, —NR$^4$(CR$^6$R$^7$)$_v$C(═NR)NR$^4$R$^5$, —O(CR$^6$R$^7$)$_v$C(═NR$^5$)NR$^4$R$^5$, —(CR$^6$R$^7$)$_v$N(R$^4$)C(═NR)NR$^4$R$^5$, —NR$^4$(CR$^6$R$^7$)$_v$N(R$^4$)C(═NR$^5$)NR$^4$R$^5$, —O(CR$^6$R$^7$)$_v$N(R$^4$)C(═NR$^5$)NR$^4$R$^5$, —NR$^4$C(═NR$^5$)NR$^4$C(═NR$^5$)NR$^4$R$^5$, —(CR$^6$R$^7$)$_v$C(═NR$^4$)NR$^5$C(═NR$^4$)NR$^4$R$^5$, —NR$^4$(CR$^6$R$^7$)$_v$C(═NR$^4$)NR$^5$C(═NR$^4$)NR$^4$R$^5$, —O(CR$^6$R$^7$)$_v$C(═NR$^4$)NR$^5$C(═NR$^4$)NR$^4$R$^5$, —NR$^4$C(═NR$^5$)NR$^4$R$^5$, —C(═NR$^4$)NR$^4$R$^5$, —C(═NR$^4$)NR$^4$C(O)R$^6$, —NR$^4$SO$_2$R$^6$, —NR$^4$C(O)R$^6$, —NR$^4$C(═O)OR$^6$, —C(O)NR$^4$R$^5$, —(CR$^6$R$^7$)$_v$C(O)NR$^4$R$^5$, -Heteroaryl-NR$^4$R$^5$, -Heterocyclyl-NR$^4$R$^5$, -Heteroaryl-N(R$^4$)C(═NR$^5$)NR$^4$R$^5$, -Heterocyclyl-N(R$^4$)C(═NR$^5$)NR$^4$R$^5$, —N(R$^4$)-Heteroaryl-NR$^4$R$^5$, —N(R$^4$)-Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(═NR$^5$)NR$^4$R$^5$, —(CR$^6$R$^7$)$_v$Heterocyclyl-N(R$^4$)C(═NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, and —O(CR$^6$R$^7$)$_v$O-Heterocyclyl.

In some embodiments is a compound of Formula I, wherein at least one Y is selected from the group consisting of fluoro, chloro, —CN, optionally substituted C$_1$-C$_6$ alkyl, —OH, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —C(O)NR$^4$(CR$^6$R$^7$)$_v$NR$^4$R$^5$, —NR$^5$C(O)NR$^4$(CR$^6$R$^7$)$_v$NR$^4$R$^5$, —NR$^5$C(═NR$^7$)NR$^4$(CR$^6$R$^7$)$_v$NR$^4$R$^5$, —N(R$^4$)C(═NR$^5$)R$^6$, —(CR$^6$R$^7$)$_v$N(R$^4$)C(═NR$^5$)R$^6$, —NR$^4$(CR$^6$R$^7$)$_v$N(R$^4$)C(═NR$^5$)R$^6$, —(CR$^6$R$^7$)$_v$C(═NR$^5$)NR$^4$R$^5$, —NR$^4$(CR$^6$R$^7$)$_v$C(═NR)NR$^4$R$^5$, —(CR$^6$R$^7$)$_v$N(R$^4$)C(═NR$^5$)NR$^4$R$^5$, —NR⁴(CR⁶R⁷)ᵥN(R⁴)C(=NR⁵)NR⁴R⁵, —NR⁴C(=NR⁵)NR⁴C(=NR⁵)NR⁴R⁵, —(CR⁶R⁷)ᵥC(=N⁴)NR⁵C(=NR⁴)NR⁴R⁵, —NR⁴(CR⁶R⁷)ᵥC(=NR⁴)NR⁵C(=NR⁴)NR⁴R⁵, —NR⁴C(=NR⁵)NR⁴R⁵, —C(=NR⁴)NR⁴R⁵, —C(=NR⁴)NR⁴C(O)R⁶, —NR⁴C(O)R⁶, —(CR⁶R⁷)ᵥC(O)NR⁴R⁵, -Heterocyclyl-NR⁴R⁵, -Heterocyclyl-N(R⁴)C(=NR⁵)NR⁴R⁵, —N(R⁴)-Heterocyclyl-NR⁴R⁵, —(CR⁶R⁷)ᵥHeterocyclyl-NR⁴R⁵, —(CR⁶R⁷)ᵥHeterocyclyl-N(R⁴)C(=NR⁵)NR⁴R⁵, —(CR⁶R⁷)ᵥHeterocyclyl, and —NR⁴(CR⁶R⁷)ᵥHeterocyclyl.

In some embodiments is a compound of Formula I, wherein at least one Y is selected from the group consisting of —NR⁴R⁵, —NR⁴C(=NR⁵)NR⁴R⁵, —C(=NR⁴)NR⁴R⁵, —N(R⁴)C(=NR⁵)R⁶, —(CR⁶R⁷)ᵥNR⁴R⁵, —(CR⁶R⁷)ᵥN(R⁴)C(=NR⁵)NR⁴R⁵, —NR⁴(CR⁶R⁷)ᵥNR⁴R⁵, —NR⁴(CR⁶R⁷)ᵥOR¹⁰, —(CR⁶R⁷)ᵥNR⁴(CR⁶R⁷)ᵥNR⁴R⁵, NR⁵C(=NR⁵)NR⁴(CR⁶R⁷)ᵥNR⁴R⁵, —NR⁴(CR⁶R⁷)ᵥN(R⁴)C(=NR⁵)NR⁴R⁵, —NR⁵C(O)CR⁶(NR⁴R⁵)(CR⁶R⁷)ᵥNR⁴R⁵, —(CR⁶R⁷)ᵥC(=NR⁵)NR⁴R⁵, —(CR⁶R⁷)ᵥN(R⁴)C(O)(CR⁶R⁷)ᵥNR⁴R⁵, —C(=NR⁴)NR⁴C(O)R⁶, —NR⁴(CR⁶R⁷)ᵥHeteroaryl, and —O(CR⁶R⁷)ᵥNR⁴R⁵.

In some embodiments is a compound of Formula I, wherein at least one Y is selected from the group consisting of -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, —N(R⁴)-Heteroaryl-NR⁴R⁵, —N(R⁴)-Heterocyclyl-NR⁴R⁵, -Heteroaryl-C(=NR)NR⁴R⁵, -Heterocyclyl-C(=NR⁵)NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, and —(CR⁶R⁷)ᵥHeterocyclyl-N(R⁴)C(=NR⁵)NR⁴R⁵.

In some embodiments is a compound of Formula I, wherein at least one Y is 2-(NR⁴R⁵)-pyridyl, 2-(NR⁴R⁵)-pyrimidinyl, 2-(NR⁴R⁵)-thiazolyl, 2-(NR⁴R⁵)-imidazolyl, 3-(NR⁴R⁵)-pyrazolyl, 3-(NR⁴R⁵)-isothiazolyl, 2-(NR⁴R⁵)-oxazolyl, piperidine, pyrrolidine, 4-amino-piperidinyl, 3-amino-pyrrolidinyl, piperazine, or 4-carboximidoyl-piperazinyl.

In some embodiments is a compound of Formula I, wherein two Y groups, together with the atoms to which they are attached form a pyrrolidine ring.

In some embodiments is a compound of Formula I, wherein p is 1 or 2.

In some embodiments is a compound of Formula I, wherein R⁴ and R⁵ are independently selected from the group consisting of hydrogen, optionally substituted C₁-C₆ alkyl, optionally substituted alkoxyalkyl, optionally substituted hydroxyalkyl, and optionally substituted heterocyclyl. In some embodiments is a compound of Formula I, wherein R⁴ and R⁵ are independently hydrogen or optionally substituted C₁-C₆ alkyl.

In some embodiments is a compound of Formula I, wherein R⁶ and R⁷ are independently selected from the group consisting of hydrogen, halogen, optionally substituted C₁-C₆ alkyl, —OH, —NR⁴R⁵, and optionally substituted heterocyclyl, or R⁶ and R⁷ taken together form an optionally substituted heterocycle with the carbon to which they are attached. In some embodiments some embodiments is a compound of Formula I, wherein R⁶ and R⁷ are independently hydrogen, fluoro, or optionally substituted C₁-C₆ alkyl.

In some embodiments is a compound of Formula I, wherein R³ is H.

In some embodiments is a compound of Formula I, wherein R³ is R³¹. In some embodiments is a compound of Formula I, wherein R³ is C₁-C₁₂ alkyl. In some embodiments is a compound of Formula I, wherein R³ is methyl, ethyl, propyl, butyl, or isopropyl.

In some embodiments is a compound of Formula I, wherein R³ is selected from the group consisting optionally substituted C₁-C₁₂ alkenyl, optionally substituted C₁-C₁₂ alkynyl, C₃-C₅ cycloalkyl, C₃-C₅ heterocycloalkyl, optionally substituted aryl, optionally substituted heteroaryl, optionally substituted alkylcycloalkyl, optionally substituted alkylheterocycloalkyl, optionally substituted alkylaryl, and optionally substituted alkylheteroaryl.

In some embodiments is a compound of Formula I, wherein R³ is optionally substituted C₁-C₁₂ alkyl, alkyloxyalkyl, acyloxyalkyl, alkyloxycarbonyloxyalkyl, cycloalkyloxycarbonyloxyalkyl, aryloxycarbonyloxyalkyl, or alkyl-[1,3]dioxol-2-one. In some embodiments is a compound of Formula I, wherein R³ is acyloxyalkyl. In some embodiments is a compound of Formula I, wherein R³ is —CH₂OC(=O)CH₃ or —CH₂OC(=O)C(CH₃)₃.

In some embodiments is a compound of Formula I, wherein R³ is —(R³⁰)qOR³¹ or —(R³⁰)qO(R³⁰)qOR³¹.

In some embodiments is a compound of Formula I, wherein R³ is selected from the group consisting of —R³⁰OC(O)R³¹, —R³⁰OC(O)OR³¹, —R³⁰OC(O)NHR³¹, and —R³⁰OC(O)N(R³¹)₂.

In some embodiments is a compound of Formula I, wherein R³ is selected from the group consisting of:

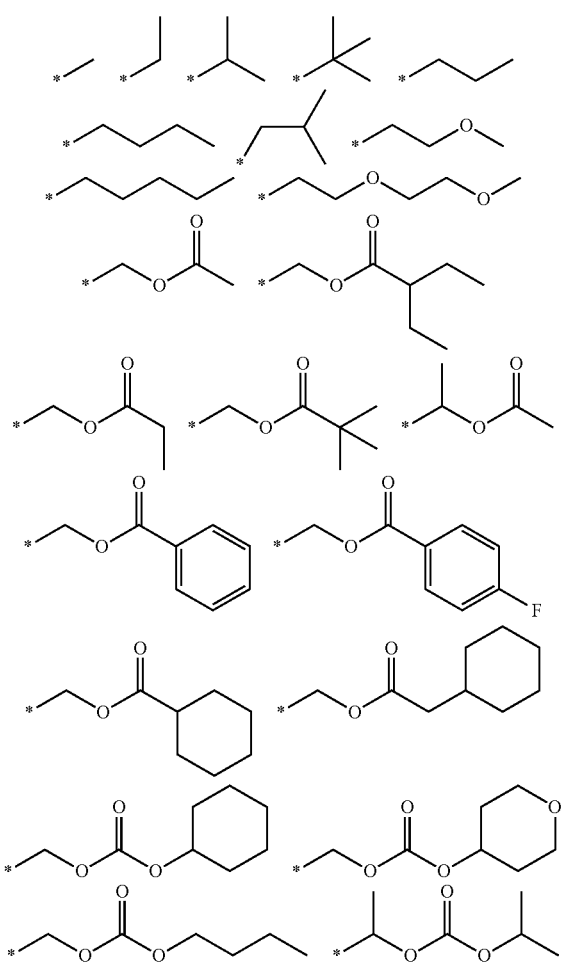

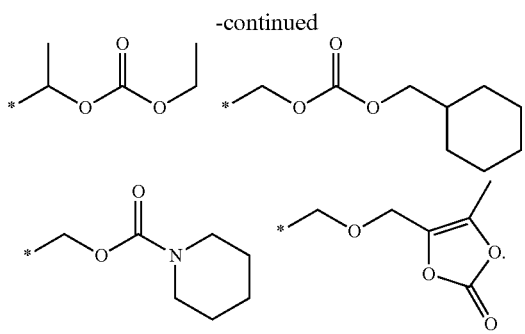

In some embodiments is a compound of Formula I, wherein $R^3$ is selected from the group consisting of methyl, ethyl, butyl, pivaloyloxymethyl, acetoxymethyl, ethoxycarbonyloxymethyl, 1-(acetoxy)ethyl, 1-(pivaloyloxy)ethyl, 1-(isopropoxycarbonyoxy)ethyl, and 1-cyclohexyloxycarbonyloxymethyl.

In certain embodiments of any of the compounds of Formula I described herein, are ring-opened compounds wherein X is

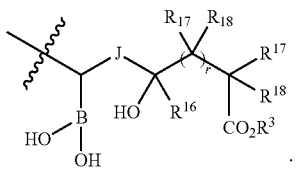

Further Forms of Compounds Disclosed Herein
Isomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may exist in an equilibrium between the "closed" cyclic form shown in Formula I and the "open" acyclic form shown in Figure Ia. In addition, the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. It should be understood that the compounds described herein also include the quaternization of any boron-containing groups they contain. Such a quaternization could result from the treatment of the Lewis acidic boron with a Lewis base to form a complex or salt. In some embodiments, water or oil-soluble or dispersible products are obtained by such quaternization.

Pharmaceutical Compositions/Formulations

In another aspect, provided herein are pharmaceutical compositions comprising a compound of Formula I as described herein, or a pharmaceutically acceptable salt, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula I and at least one pharmaceutically acceptable inactive ingredient. In some embodiments, the compounds described herein are administered as pharmaceutical compositions in which a compound of Formula I is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combinations thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula I are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula I as an active ingredient in free-acid or free-base form, or in a pharmaceutically acceptable salt form. In addition, the methods and pharmaceutical compositions described herein include the use of N-oxides (if appropriate).

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds according to Formula I may be used in combination with one or more antibiotics in the treatment of bacterial infections. Such antibiotics may be administered, by a route and in an amount commonly used therefore, contemporaneously or sequentially with a compound of Formula I. When a compound of Formula I is used contemporaneously with one or more antibiotic, a pharmaceutical composition in unit dosage form containing such other drugs and the compound of the present invention is preferred. However, the combination therapy may also include therapies in which the compound of Formula I and one or more antibiotics are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound according to Formula I. In some embodiments, a pharmaceutical composition comprising a compound of Formula I further comprises a beta-lactam antibiotic. In certain embodiments, the beta-lactam antibiotic is a penicillin, cephalosporin, carbapenem, monobactam, bridged monobactam, or a combination thereof.

The above combinations include combinations of a compound of Formula I not only with one antibiotic, but also with two or more antibiotics. Likewise, compounds of Formula I, either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound of Formula I. When a compound of Formula I is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of Formula I. The weight ratio of the compound of Formula I to the second active ingredient may be varied and will depend upon the effective dose of each ingredient. Generally, an effective dose of each will be used.

In some embodiments, the compounds according to Formula I are used in combination with one or more antibiotics in the treatment of bacterial infections. In certain embodiments, the bacterial infection is an upper or lower respiratory tract infection, a urinary tract infection, an intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, and ticarcillin. Penems include, but are not limited to, faropenem. Carbapenems include, but are not limited to, biapenem, ertapenem, doripenem, imipenem, meropenem, panipenem. Cephalosprins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, and loracarbef. Monobactams include, but are not limited to, aztreonam, carumonam, nocardicin A, and tigemonam.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula I and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e g, Page, *Biochem J*, 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221:505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g, Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art. Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor of Formula I are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound of Formula I is administered to an experimental cell culture in vitro to prevent the growth of beta-lactam resistant bacteria. In certain other embodiments, a compound of Formula I is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound of Formula I, or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a beta-lactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In some embodiments, the infection that is treated or prevented comprises a bacteria that includes *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides*

*ovalus, Bacteroides thetaiotaomicron, Bacteroides uniformis, Bacteroides eggerthii,* or *Bacteroides splanchnicus.*

Preparation of Compounds

Described herein are compounds of Formula I that inhibit the activity of beta-lactamases, and processes for their preparation. Also described herein are pharmaceutically acceptable salts of such compounds. Pharmaceutical compositions comprising at least one such compound or a pharmaceutically acceptable salt of such compound, and a pharmaceutically acceptable excipient are also provided.

Compounds of Formula I may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in U.S. Pat. No. 8,680,136; WO 01/01982901; WO 2009/064414; Arnold et al. *Bioorganic & Medicinal Chemistry Letters* 10 (2000) 2167-2170; and Burchat et al. *Bioorganic & Medicinal Chemistry Letters* 12 (2002) 1687-1690; which are all incorporated by reference in their entirety.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

The following compounds of Formula I are shown in Table 1 to enable those of skill in the art to more clearly understand and to practice the present invention. They should not be considered as limiting the scope of the invention, but merely as illustrative and representative thereof.

TABLE 1

Examples of Compounds

| Example | Structure | MW |
|---|---|---|
| 1 | 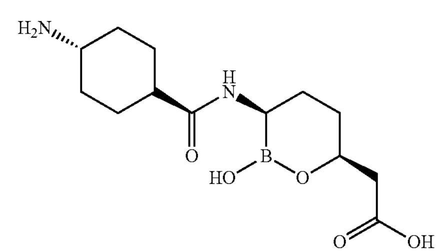 | 298 |
| 2 | 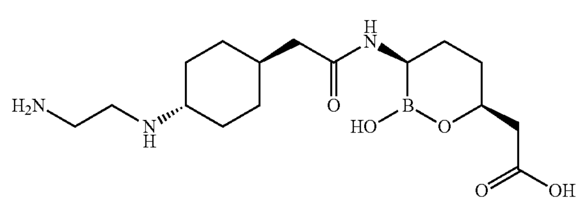 [SMILES: NCCN[C@H]1CC[C@H](CC(=O)N[C@H]2CC[C@@H](CC(=O)O)OB2O)CC1] | 355 |
| 3 | 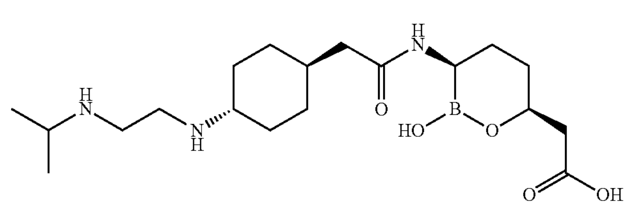 [SMILES: CC(C)NCCN[C@H]1CC[C@H](CC(=O)N[C@H]2CC[C@@H](CC(=O)O)OB2O)CC1] | 397 |

TABLE 1-continued

Examples of Compounds

| Example | Structure | MW |
|---------|-----------|-----|
| 4 | 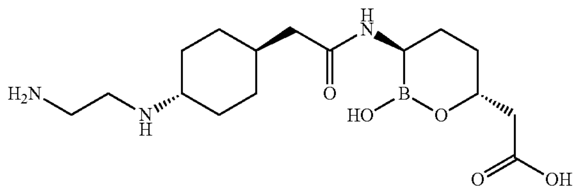 [SMILES: NCCN[C@H]1CC[C@H](CC(=O)N[C@H]2CC[C@H](CC(=O)O)OB2O)CC1] | 355 |
| 5 | 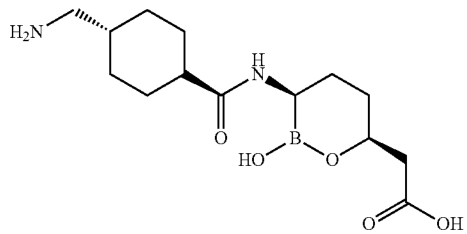 | 312 |
| 6 | 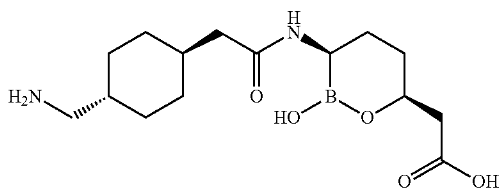 [SMILES: NC[C@H]1CC[C@H](CC(=O)N[C@H]2CC[C@@H](CC(=O)O)OB2O)CC1] | 326 |
| 7 | 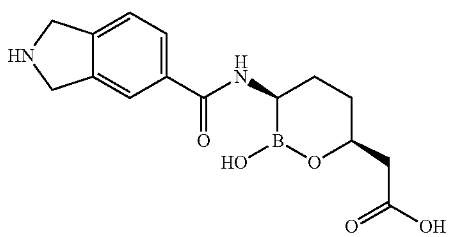 [SMILES: O=C(O)C[C@@H]1CC[C@H](NC(=O)c2ccc3c(c2)CNC3)B(O)O1] | 318 |
| 8 | 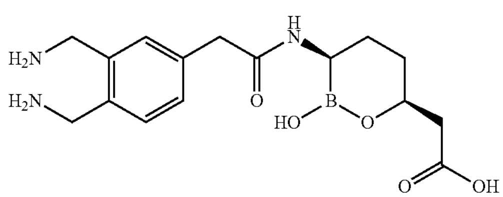 [SMILES: NCc1ccc(CC(=O)N[C@H]2CC[C@@H](CC(=O)O)OB2O)cc1CN] | 349 |
| 9 | 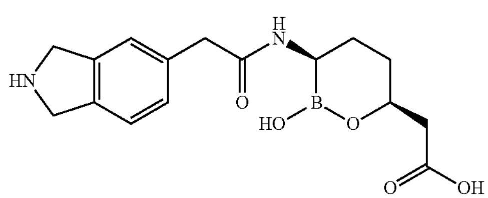 [SMILES: O=C(O)C[C@@H]1CC[C@H](NC(=O)Cc2ccc3c(c2)CNC3)B(O)O1] | 332 |
| 10 | 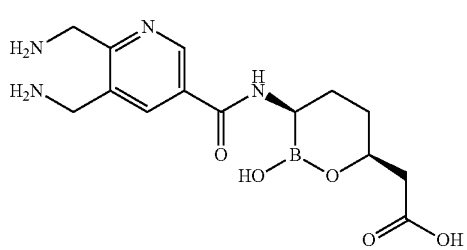 [SMILES: NCc1cc(C(=O)N[C@H]2CC[C@@H](CC(=O)O)OB2O)cnc1CN] | 336 |

TABLE 1-continued

Examples of Compounds

| Example | Structure | MW |
|---------|-----------|-----|
| 11 | 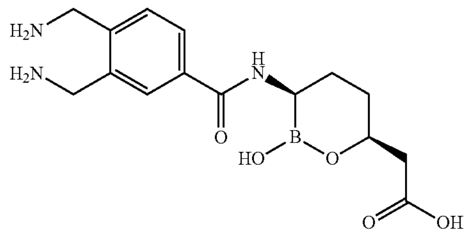 [SMILES: NCc1ccc(C(=O)N[C@H]2CC[C@@H](CC(=O)O)OB2O)cc1CN] | 335 |
| 12 | 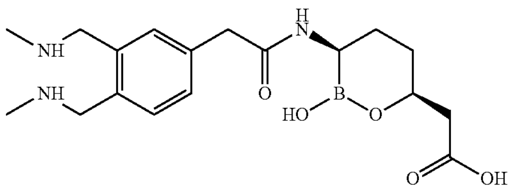 [SMILES: CNCc1ccc(CC(=O)N[C@H]2CC[C@@H](CC(=O)O)OB2O)cc1CNC] | 377 |
| 13 | 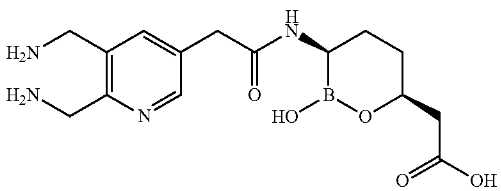 [SMILES: NCc1cc(CC(=O)N[C@H]2CC[C@@H](CC(=O)O)OB2O)cnc1CN] | 350 |
| 14 | 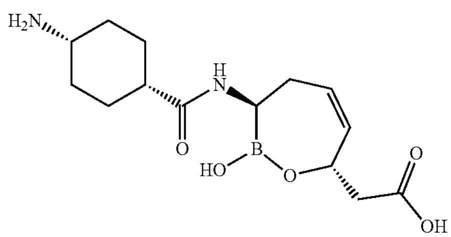 [SMILES: N[C@H]1CC[C@@H](C(=O)N[C@H]2CC=C[C@H](CC(=O)O)OB2O)CC1] | 310 |
| 15 | 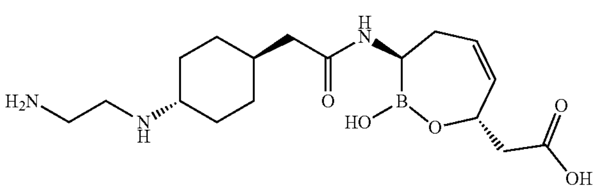 [SMILES: NCCN[C@H]1CC[C@H](CC(=O)N[C@H]2CC=C[C@H](CC(=O)O)OB2O)CC1] | 367 |
| 16 | 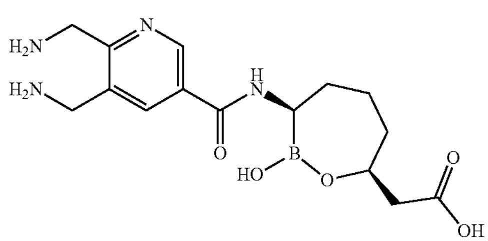 [SMILES: NCc1cc(C(=O)N[C@H]2CCC[C@@H](CC(=O)O)OB2O)cnc1CN] | 350 |
| 17 | 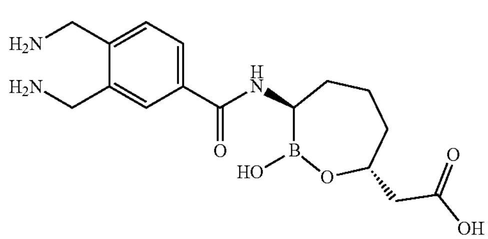 [SMILES: NCc1ccc(C(=O)N[C@H]2CCC[C@H](CC(=O)O)OB2O)cc1CN] | 347 |

TABLE 1-continued

Examples of Compounds

| Example | Structure | MW |
|---|---|---|
| 18 | 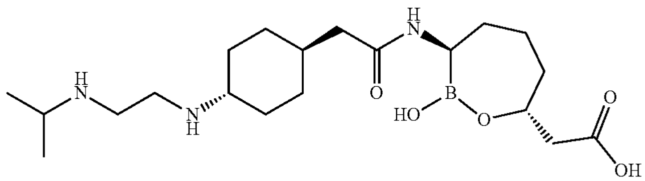 [SMILES: CC(C)NCCN[C@H]1CC[C@H](CC(=O)N[C@H]2CCC[C@H](CC(=O)O)OB2O)CC1] | 411 |
| 19 | 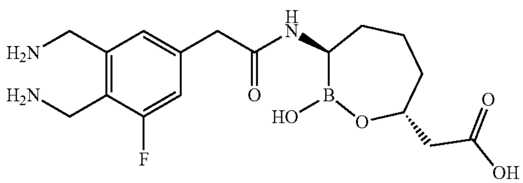 [SMILES: NCc1cc(CC(=O)N[C@H]2CCC[C@H](CC(=O)O)OB2O)cc(F)c1CN] | 381 |
| 20 | 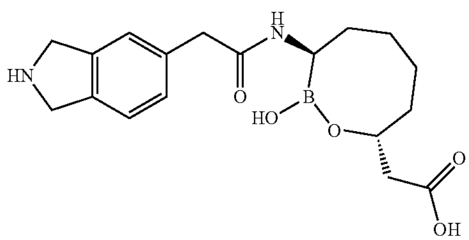 [SMILES: O=C(O)C[C@H]1CCCC[C@H](NC(=O)Cc2ccc3c(c2)CNC3)B(O)O1] | 360 |
| 21 | 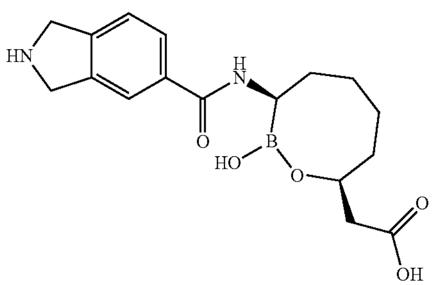 [SMILES: O=C(O)C[C@@H]1CCCC[C@H](NC(=O)c2ccc3c(c2)CNC3)B(O)O1] | 346 |
| 22 | 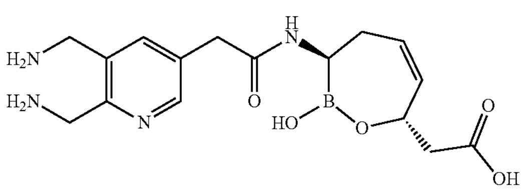 [SMILES: NCc1cc(CC(=O)N[C@H]2CC=C[C@H](CC(=O)O)OB2O)cnc1CN] | 362 |
| 23 | 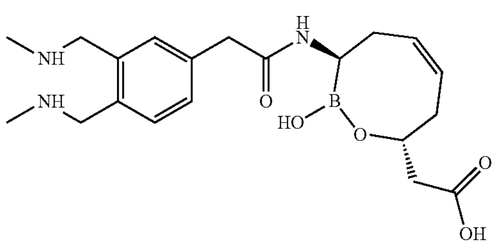 [SMILES: CNCc1ccc(CC(=O)N[C@H]2C/C=C\C[C@H](CC(=O)O)OB2O)cc1CNC] | 403 |

TABLE 1-continued

Examples of Compounds

| Example | Structure | MW |
|---------|-----------|-----|
| 24 | 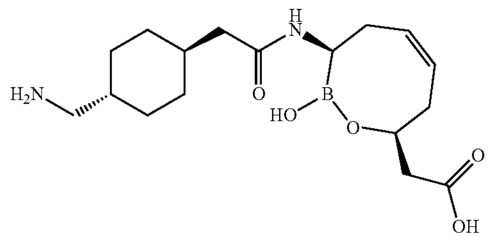 [SMILES: NC[C@H]1CC[C@H](CC(=O)N[C@H]2C/C=C\C[C@@H](CC(=O)O)OB2O)CC1] | 352 |
| 25 | 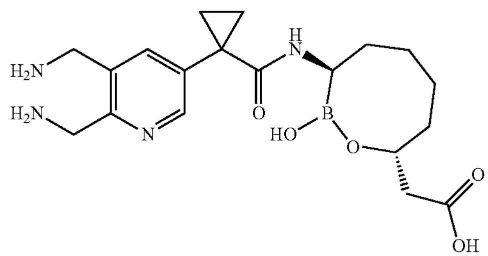 [SMILES: NCc1cc(C2(C(=O)N[C@H]3CCCC[C@H](CC(=O)O)OB3O)CC2)cnc1CN] | 404 |
| 26 | 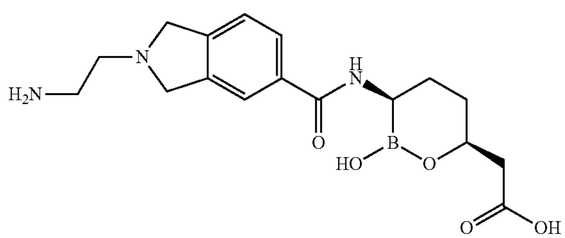 [SMILES: NCCN1Cc2ccc(C(=O)N[C@H]3CC[C@@H](CC(=O)O)OB3O)cc2C1] | 361 |
| 27 | 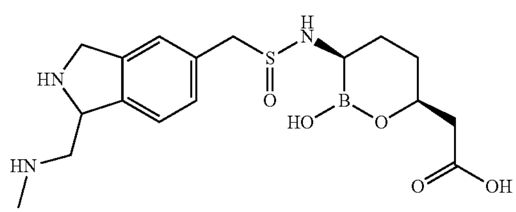 [SMILES: CNCC1NCc2cc(CS(=O)N[C@H]3CC[C@@H](CC(=O)O)OB3O)ccc21] | 375 |
| 28 | 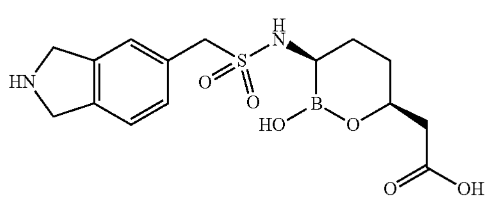 [SMILES: O=C(O)C[C@@H]1CC[C@H](NS(=O)(=O)Cc2ccc3c(c2)CNC3)B(O)O1] | 368 |

EXAMPLE 29:

Parenteral Composition Of A Compound Of Formula I

To prepare a parenteral pharmaceutical composition suitable for administration by injection, 100 mg of a compound of Formula I, or a water soluble pharmaceutically acceptable salt thereof, is dissolved in DMSO and then mixed with 10 ml of 0.9% sterile saline solution. The mixture is incorporated into a dosage unit suitable for administration by injection.

EXAMPLE 30:

Oral Composition Of A Compound Of Formula I

To prepare a pharmaceutical composition for oral delivery, 400 mg of a compound of Formula I and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

BIOLOGICAL EXAMPLES

Example I:

Experimental Method For β-Lactamase Enzyme Assays

Isolation of β-Lactamases.

For SHV-5, Kpc-2, p99AmpC and OXA-1 β-lactamases, *E. coli* BL21(DE3) bacterial cells carrying expression plasmids (expressed as native untagged proteins) for the individual β-lactamases were grown in 1 L of Superbroth (Teknova Inc. Hollister, Calif.) supplemented with 100 μg/ml kanamycin selection and 1× 5052 (0.5% glycerol, 0.05% glucose and 0.2% α-lactose) at 35° C. for 18-20 hours. Cells were harvested by centrifugation (4,000×g, 4° C., 20 min), resuspended in 50 ml of 10 mM HEPES pH 7.5 (1/20 of the initial volume). The cells were lysed by sonication (5 pulses of 45 seconds) at 45 W on ice. The lysates were clarified by centrifugation at 10,000×g for 40 minutes at 4° C. Samples were diluted 5-fold in 50 mM sodium acetate pH 5.0, stored overnight at 4° C., after which they were centrifuged at 10,000×g for 30 minutes to clarify, and filtered through 0.45 m filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre-equilibrated in 50 mM Hepes pH 7.5, 150 mM NaCl. Active fractions were pooled concentrated, quantitated by BCA protein determination (Thermo Scientific, Rockford, Ill.), dialyzed into PBS and frozen at −80° C. in 20% glycerol until use.

For Vim-2 metallo β-lactamase, the procedure was identical with the following exceptions, first the protein was not pH adjusted to pH 5 with 50 mM sodium acetate, second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run ($3^{rd}$ step) on the Q sepharose anion exchange column to achieve acceptable purity (>90%).

β-Lactamase Inhibition.

To determine the level of inhibition of β-lactamase enzymes, compounds are diluted in PBS at pH 7.4 to yield concentrations ranging from 100 to 0.00005 μM in 96-well microtiter plates. An equal volume of diluted enzyme stock is added, and the plates are incubated at 37° C. for 15 min. Nitrocefin is used as substrate for p99 AmpC, VIM-2 and OXA-1 and dispensed into each well at a final concentration of 100 μM. Absorbance at 486 nm is immediately monitored for 10 min using a Biotek Powerwave XS2 microplate spectrophotometer using the GEN5 software package (Biotek Instruments, Winooski Vt.). In an analogous fashion, imipenem is used as substrate for Kpc-2 and Cefotaxime is used for SHV-5, while changes in absorbance upon hydrolysis of the β-lactam ring are monitored at 300 nm and 260 nm respectively in UV-transparent 96-well microtiter assay plates. Maximum rates of hydrolysis are compared to those in control wells (without inhibitors), and percentages of enzyme inhibition are calculated for each concentration of inhibitor. The concentration of inhibitor needed to reduce the initial rate of hydrolysis of substrate by 50% ($IC_{50}$) is calculated as the residual activity of β-lactamase at 486 nm using GraFit version 7 kinetics software package (Erithacus Software, Surrey, UK).

Example II:

In Vitro Antibacterial Assays of β-Lactamase Inhibition

To determine the ability of test compounds to potentiate the inhibition of the growth of bacterial strains that produce beta-lactamase enzymes, classic cell based broth microdilution MIC assays are employed. Six bacteria strains producing beta-lactamase enzymes are used: *E. coli* expressing the Class A Extended Spectrum Beta-Lactamase (ESBL) CTX-M-15, *E. cloacae* expressing the Class C P99, *K. pneumoniae* expressing the Class A carbapenemase KPC-3, *P. aeruginosa* expressing the Class B carbapenemase VIM-2, *K. pneumoniae* expressing the class A carbapenemase KPC-2 and the class B carbapenemase VIM-4, and *S. aureus* producing the Class A penicillinase PC-1. The assay is conducted in Cation Adjusted Mueller Hinton Broth (CAMHB, BD #212322, BD Diagnostic Systems, Sparks, Md.). Bacteria strains are grown for 3-5 hours in CAMBH broth. Test compounds are added to a microtiter plate in 2-fold serial dilutions in CAMHB in a final concentration range of 32 μg/mL to 0.25 μg/ml. An overlay of CAMHB containing a Beta-lactam is added to the compounds at a final static concentration of 4 μg/mL. Ceftazidime (CAZ, Sigma# C3809-1G, Sigma-Aldrich, St. Louis, Mo.) is used as the partner antibiotic for *E. coli* expressing Ambler Class A ESBL CTX-M-15 (MIC alone>128 μg/ml), and *E. cloacae* expressing Class C P99 (MIC alone=128 μg/mL). Meropenem (Mero, USP #1392454, U.S. Pharmacopeia, Rockville, Md.) is used as the partner antibiotic for *K. pneumoniae* expressing Ambler Class A carbapenemase KPC-3 (MIC alone>128 μg/mL), *P. aeruginosa* expressing Class A carbapenemase VIM-2 (MIC alone=16 μg/mL), and

*K. pneumoniae* expressing the Ambler Class A carbapenemase KPC-2 and Ambler Class B carbapenemase VIM-4 (MIC alone=64 µg/mL). Piperacillin (Pip, Fisher # ICN15626801, MP Biomidicals, Solon, Ohio) is used as the partner antibiotic for *S. aureus* producing the Class A penicillinase PC-1 (MIC alone=64 µg/ml). Titration of test compounds with MIC readout indicates the concentration of test article needed to sufficiently inhibit beta-lactamase enzyme activity and protect the intrinsic antibacterial activity of the beta-lactam. In addition to the titration of test compounds, the MICs of a panel of control beta-lactams is also tested to ensure the strains are behaving consistently from test to test. Once the test compound and antibiotics are added the plates can be inoculated according to CLSI broth microdilution method. After inoculation the plates are incubated for 16-20 hours at 37° C. then the Minimal Inhibitory Concentration (MIC) of the test compound is determined visually.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A compound of Formula (I) or a pharmaceutically acceptable salt, N-oxide, or isomer thereof:

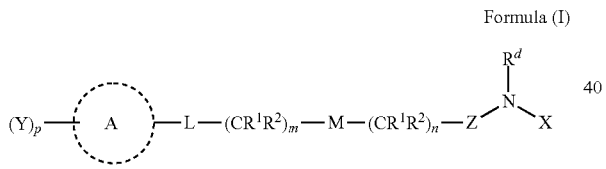

Formula (I)

wherein:
L is a bond;
M is a bond;
m is 0;
n is 0;
p is 1, 2, 3, or 4;
Z is —C(=O)—, —C(=S), or —S(O)$_2$—;
A is CycA, ArA, or HetA, wherein:
  CycA is an optionally substituted 3-10 membered non-aromatic carbocycle, wherein an optional olefin functionality of the non-aromatic carbocycle is not directly attached to an oxygen, sulfur, or nitrogen substituent;
  ArA is an aromatic or heteroaromatic ring system optionally substituted with one or more substituents selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —OR$^{10}$, and —SR$^{10}$;
  HetA is an optionally substituted non-aromatic heterocyclic ring system;

each $R^1$ and $R^2$ is independently selected from the group consisting of hydrogen, fluoro, chloro, bromo, optionally substituted $C_1$-$C_6$ alkyl, optionally substituted $C_3$-$C_6$ cycloalkyl, —OH, —OR$^{10}$, —SR$^{10}$, and —NR$^4$R$^5$,
or $R^1$ and $R^2$ taken together form an oxo, oxime, or an optionally substituted carbocycle or optionally substituted heterocycle with the carbon to which they are attached;
each $R^d$, $R^4$, and $R^5$ is independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or $R^4$ and $R^5$ taken together form an optionally substituted heterocycle with the nitrogen to which they are attached;
each $R^{10}$ is independently selected from the group consisting of $C_1$-$C_6$ alkyl and optionally substituted $C_3$-$C_6$ cycloalkyl;
each Y, provided that Y is not attached directly to a heteroatom of HetA, is selected from the group consisting of:
  fluoro, chloro, bromo, —CN, $C_1$-$C_6$ alkyl, optionally substituted $C_3$-$C_6$ cycloalkyl, optionally substituted heterocycle, optionally substituted aryl, optionally substituted heteroaryl, —OH, —OR$^{10}$, —SR$^{10}$, —NR$^4$R$^5$, —(CR$^6$R$^7$)$_v$NR$^4$R$_5$, —NR$^4$(CR$^6$R$^7$)$_v$NR$^4$R$^5$, —O(CR$^6$R$^7$)$_v$NR$^4$R$^5$, —S(O)$_{0,1,2}$(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —(CR$^6$R$^7$)$_v$NR$^4$(CR$^6$R$^7$)$_v$NR$^4$R$^5$, —NR$^4$(CR$^6$R$^7$)$_v$OR$^{10}$, —NR$^4$(CR$^6$R$^7$)$_v$S(O)$_{0,1,2}$R$^{10}$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —S(O)$_{0,1,2}$(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —S(O)$_{0,1,2}$(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —S(O)$_{0,1,2}$(CR$^6$R$^7$)$_v$N(R$^4$)C(=NR$^5$)NR$^4$R$^5$, —NR$^4$C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)$_v$C(=NR$^4$)NR$^5$C(=NR$^4$)NR$^4$R$^5$, —S(O)$_{0,1,2}$—(CR$^6$R$^7$)$_v$C(=NR$^4$)NR$^5$C(=NR$^4$)NR$^4$R$^5$, —NR$^4$C(=NR$^5$)NR$^4$R$^5$, —C(=NR$^4$)NR$^4$R$^5$, —C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, Heteroaryl-N(R$^4$)C(=NR$^5$)NR$^4$R$^5$, -Heterocyclyl-N(R$^4$)C(=NR$^5$)NR$^4$R$^5$, —N(R$^4$)-Heteroaryl-NR$^4$R$^5$, —N(R$^4$)-Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR⁶R⁷)ᵥHeteroaryl-N(R⁴)C(=NR⁵)NR⁴R⁵,
—(CR⁶R⁷)ᵥHeterocyclyl-N(R⁴)C(=NR⁵)NR⁴R⁵,
—(CR⁶R⁷)ᵥHeterocyclyl, —O-Heteroaryl,
—O-Heterocyclyl, —NR⁴(CR⁶R⁷)ᵥHeteroaryl,
—NR⁴(CR⁶R⁷)ᵥHeterocyclyl, —O(CR⁶R⁷)ᵥHeteroaryl, —O(CR⁶R⁷)ᵥHeterocyclyl, —NR⁴(CR⁶R⁷)ᵥNR⁵-Heteroaryl, —NR⁴(CR⁶R⁷)ᵥNR⁵-Heterocyclyl, —O(CR⁶R⁷)ᵥNR⁵-Heteroaryl, —O(CR⁶R⁷)ᵥNR⁵-Heterocyclyl, —O(CR⁶R⁷)ᵥO-Heterocyclyl, —NR⁴R⁵R⁹⁺Q⁻, —(CR⁶R⁷)ᵥNR⁴R⁵R⁹⁺Q⁻, —NR⁴(CR⁶R⁷)ᵥNR⁴R⁵R⁹⁺Q⁻, —NR⁴R⁹⁺(CR⁶R⁷)ᵥNR⁴R⁵R⁹⁺Q⁻₂, —(CR⁶R⁷)ᵥ(T)⁺Q⁻, and —O(CR⁶R⁷)ᵥNR⁴R⁵R⁹⁺Q⁻; or each Y, in the case where Y is attached directly to a heteroatom of HetA, is selected from the group consisting of:

—(CR⁶R⁷)ᵥNR⁴R⁵, —S(O)₁,₂(CR⁶R⁷)ᵥNR⁴R⁵, —C(O)(CR⁶R⁷)ᵥNR⁴R⁵, —(CR⁶R⁷)ᵥN(R⁴)C(O)(CR⁶R⁷)ᵥNR⁴R⁵, —(CR⁶R⁷)ᵥNR⁴(CR⁶R⁷)ᵥNR⁴R⁵, —NR⁴(CR⁶R⁷)ᵥOR¹⁰, —(CR⁶R⁷)ᵥS(O)₀,₁,₂R¹⁰, —C(O)NR⁴(CR⁶R⁷)ᵥNR⁴R⁵, —S(O)₁,₂NR⁴(CR⁶R⁷)ᵥNR⁴R⁵, —C(=NR⁷)NR⁴(CR⁶R⁷)ᵥNR⁴R⁵, —C(=NR⁵)R⁶, —(CR⁶R⁷)ᵥN(R⁴)C(=NR⁵)R⁶, —S(O)₁,₂(CR⁶R⁷)ᵥN(R⁴)C(=NR⁵)R⁶, —(CR⁶R⁷)ᵥN(R⁵)NR⁴R⁵, —(CR⁶R⁷)ᵥC(=NR⁵)NR⁴R⁵, —S(O)₁,₂(CR⁶R⁷)ᵥC(=NR⁵)NR⁴R⁵, —(CR⁶R⁷)ᵥN(R⁴)C(=NR⁵)NR⁴R⁵, —S(O)₁,₂(CR⁶R⁷)ᵥN(R⁴)C(=NR⁵)NR⁴R⁵, —C(=NR⁵)NR⁴C(=NR⁵)NR⁴R⁵, —(CR⁶R⁷)ᵥC(=NR⁴)NR⁵C(=NR⁴)NR⁴R⁵, —S(O)₁,₂(CR⁶R⁷)ᵥC(=NR⁴)NR⁵C(=NR⁴)NR⁴R⁵, —C(=NR⁴)NR⁴R⁵, —C(=NR⁴)NR⁴C(O)R⁶, —SO₂R⁶, —C(O)R⁶, —C(=O)OR⁶, —C(O)NR⁴R⁵, —(CR⁶R⁷)ᵥC(O)NR⁴R⁵, —SO₂NR⁴R⁵, -aryl, -heteroaryl, —C(O)N(R⁴)-Heteroaryl-NR⁴R⁵, -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, -Heteroaryl-NR⁴R⁵, -Heterocyclyl-NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, —(CR⁶R⁷)ᵥHeterocyclyl-N(R⁴)C(=NR⁵)NR⁴R⁵, —(CR⁶R⁷)ᵥHeteroaryl, —(CR⁶R⁷)ᵥHeterocyclyl, —(CR⁶R⁷)ᵥNR⁵-Heteroaryl, —(CR⁶R⁷)ᵥNR⁵-Heterocyclyl, —(CR⁶R⁷)ᵥO-Heterocyclyl, —R⁹⁺Q⁻, —(CR⁶R⁷)ᵥNR⁴R⁵R⁹⁺Q⁻, —R⁹⁺(CR⁶R⁷)ᵥNR⁴R⁵R⁹⁺Q⁻₂ and —(CR⁶R⁷)ᵥ(T)⁺Q⁻;

wherein:
T is pyridin-1-yl, pyrimidin-1-yl, or thiazol-3-yl;
Q is a pharmaceutically acceptable counterion;
each R⁶ and R⁷ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —OR¹⁰, —SR¹⁰, —NR⁴R⁵, —NR⁴C(O)R⁵, —C(O)NR⁴R⁵, —NR⁴SO₂R⁵, optionally substituted heterocyclyl, optionally substituted aryl, and optionally substituted heteroaryl;
or R⁶ and R⁷ taken together form an oxo, oxime, or an optionally substituted carbocycle or an optionally substituted heterocycle with the carbon to which they are attached;
R⁹ is optionally substituted $C_1$-$C_6$ alkyl;
v is 1-4; and
w is 2-4;

or two Ys taken together with the carbon atoms to which they are attached form an optionally substituted carbocycle, an optionally substituted heterocycle, or a carbonyl group;

X is

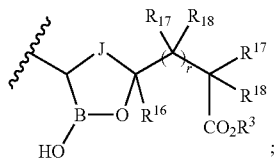

J is a 1-4 atom alkylene or 1-4 atom alkenylene, optionally substituted by one or more substituents selected from the group consisting of Cl, F, CN, CF₃, —R¹⁹, —OR¹⁹, —C(=O)NR¹⁹R²⁰, and —C(=O)OR¹⁹, wherein said 1-4 atom alkylene or 1-4 atom alkenylene is optionally fused to an optionally substituted aryl, optionally substituted heteroaryl, optionally substituted carbocyclyl, or optionally substituted heterocyclyl;

R³ is selected from the group consisting of H, R³¹, —(R³⁰)qOR³¹, —(R³⁰)qO(R³⁰)qOR³¹, —R³⁰OC(O)R³¹, —R³⁰OC(O)OR³¹, —R³⁰OC(O)NHR³¹, —R³⁰OC(O)N(R³¹)₂, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, and optionally substituted alkyl-[1,3]dioxol-2-one;

each R³⁰ is independently —CH₂—, —CH(CH₃)—, —C(CH₃)₂—, or optionally substituted 1,1'-cyclopropylene;

R³¹ is selected from the group consisting of optionally substituted $C_1$-$C_{12}$ alkyl, optionally substituted $C_1$-$C_{12}$ alkenyl, optionally substituted $C_1$-$C_{12}$ alkynyl, $C_3$-$C_8$ cycloalkyl, $C_3$-$C_8$ heterocycloalkyl, optionally substituted aryl, optionally substituted heteroaryl, optionally substituted alkylcycloalkyl, optionally substituted alkylheterocycloalkyl, optionally substituted alkylaryl, and optionally substituted alkylheteroaryl;

each q is independently 2, 3, 4, 5, or 6;

R¹⁶ is selected from a group consisting of H, —C₁-C₉alkyl, —C₂-C₉alkenyl, —C₂-C₉alkynyl, carbocyclyl, —C₁-C₉alkylR²¹, —C₂-C₉alkenylR²¹, —C₂-C₉alkynylR²¹, carbocyclylR²¹, —C(=O)OR¹⁹, —C₁-C₉alkylC(=O)OR¹⁹, —C₂-C₉alkenylC(=O)OR¹⁹, —C₂-C₉alkynylC(=O)OR¹⁹, carbocyclylC(=O)OR¹⁹, or alternatively:
(i) R¹⁶ and an R¹⁷ are taken together with the atoms to which they are attached to form a substituted or unsubstituted carbocyclyl or substituted or unsubstituted heterocyclyl, or
(ii) R¹⁶ and a carbon atom in J are taken together with intervening atoms to form a substituted or unsubstituted carbocyclyl or substituted or unsubstituted heterocyclyl;

each R¹⁷ is independently selected from a group consisting of H, halo, —C₁-C₉alkyl, —C₂-C₉alkenyl, —C₂-C₉alkynyl, NR¹⁹R²⁰, —OR¹⁹, —C₁-C₉alkylC(=O)OR¹⁹, —C₂-C₉alkenylC(=O)OR¹⁹, —C₂-C₉alkynylC(=O)OR¹⁹, carbocyclylC(=O)OR¹⁹, or independently:
(i) R¹⁷ and an R¹⁸ are taken together with the atoms to which they are attached to form a substituted or unsubstituted carbocyclyl or substituted or unsubstituted heterocyclyl, or (ii) an $R^{17}$ and a carbon atom in J are taken together with intervening atoms to form a substituted or unsubstituted carbocyclyl or substituted or unsubstituted heterocyclyl;

each $R^{18}$ is independently selected from a group consisting of H, halo, —$C_2$-$C_9$alkenyl, —$C_2$-$C_9$alkynyl, $NR^{19}R^{20}$, —$OR^{19}$, —$C_1$-$C_9$alkylC(=O)$OR^{19}$, —$C_2$-$C_9$alkenylC(=O)$OR^{19}$, —$C_2$-$C_9$alkynylC(=O)$OR^{19}$, carbocyclylC(=O)$OR^{19}$, or a geminal $R^{17}$ and $R^{18}$ together form —$C_2$-$C_9$alkenylC(=O)$OR^{19}$;

each $R^{19}$ is independently selected from a group consisting of H, —$C_1$-$C_9$alkyl, —$C_2$-$C_9$alkenyl, —$C_2$-$C_9$alkynyl, carbocyclyl, —$C_1$-$C_9$alkyl$R^{21}$, —$C_2$-$C_9$alkenyl$R^{21}$, —$C_2$-$C_9$alkynyl$R^{21}$, carbocyclyl$R^{21}$, substituted or unsubstituted aryl, substituted or unsubstituted heteroaryl, substituted or unsubstituted carbocyclyl, and substituted or unsubstituted heterocyclyl;

each $R^{20}$ is independently selected from a group consisting of H, —$C_1$-$C_9$alkyl, —$OR^{19}$, —CH(=NH), —C(=O)$OR^{19}$, substituted or unsubstituted aryl, substituted or unsubstituted heteroaryl, substituted or unsubstituted carbocyclyl, and substituted or unsubstituted heterocyclyl;

each $R^{21}$ is independently selected from a group consisting of substituted or unsubstituted aryl, substituted or unsubstituted heteroaryl, substituted or unsubstituted carbocyclyl, and substituted or unsubstituted heterocyclyl; and r is 0 or 1, wherein each —$C_1$-$C_9$alkyl, —$C_2$-$C_9$alkenyl, and —$C_2$-$C_9$alkynyl of $R^{16}$, $R^{17}$, $R^{18}$, $R^{19}$, $R^{20}$, and $R^{21}$ is independently optionally substituted.

2. The compound of claim 1, wherein:

X is

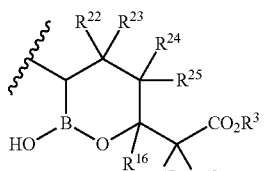

and $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$; or X is

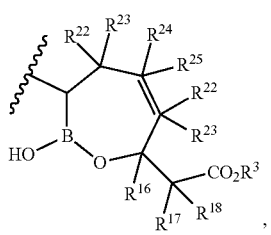

and each $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$; or X is

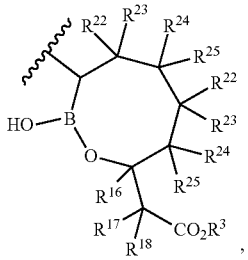

and each $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$; or X is

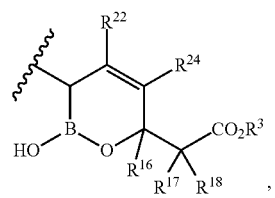

and $R^{22}$ and $R^{24}$ are independently H, Cl, F, CN, $CF_3$, —$R^{19}$, —$OR^{19}$, —C(=O)$NR^{19}R^{20}$, or —C(=O)$OR^{19}$; or X is

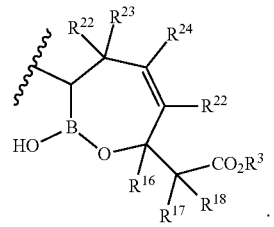

and each $R^{22}$, $R^{23}$, and $R^{24}$ are independently H, Cl, F, CN, $CF_3$, —$R^{19}$, —$OR^{19}$, —C(=O)$NR^{19}R^{20}$, or —C(=O)$OR^{19}$; or X is

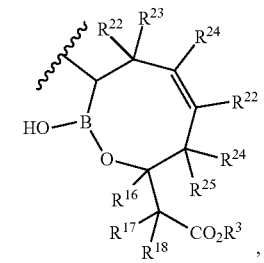

and each $R^{22}$, $R^{23}$, $R^{24}$, and $R^{25}$ are independently H, Cl, F, CN, $CF_3$, —$R^{19}$, —$OR^{19}$, —C(=O)$NR^{19}R^{20}$, or —C(=O)$OR^{19}$.

3. The compound of claim 1, wherein $R^{16}$, $R^{17}$, and $R^{18}$ are H.

4. The compound of claim 1, wherein $R^d$ is hydrogen.

5. The compound of claim 1, wherein Z is —C(=O)—.

6. The compound of claim 1, wherein A is HetA; and HetA is selected from the group consisting of piperidine, piperazine, pyrrolidine, tetrahydropyran, and tetrahydrofuran.

7. The compound of claim 1, wherein A is cyclohexyl, phenyl, or pyridyl.

8. The compound of claim 1, wherein at least one Y is selected from the group consisting of —NR$^4$R$^5$, —NR$^4$C(=NR$^5$)NR$^4$R$^5$, —C(=NR$^4$)NR$^4$R$^5$, —N(R$^4$)C(=NR$^5$)R$^6$, —(CR$^6$R$^7$)$_v$NR$^4$R$^5$, —(CR$^6$R$^7$)$_v$N(R$^4$)C(=NR$^5$)NR$^4$R$^5$, —NR$^4$(CR$^6$R$^7$)$_v$NR$^4$R$^5$, —NR$^4$(CR$^6$R$^7$)$_v$OR$^{10}$, —(CR$^6$R$^7$)$_v$NR$^4$(CR$^6$R$^7$)$_v$NR$^4$R$^5$, —NR$^5$C(=NR$^5$)NR$^4$(CR$^6$R$^7$)$_v$NR$^4$R$^5$, —NR$^4$(CR$^6$R$^7$)$_v$N(R$^4$)C(=NR$^5$)NR$^4$R$^5$, —NR$^5$C(O)CR$^6$(NR$^4$R$^5$)(CR$^6$R$^7$)$_v$NR$^4$R$^5$, —(CR$^6$R$^7$)$_v$C(=NR$^5$)NR$^4$R$^5$, —(CR$^6$R$^7$)$_v$N(R$^4$)C(O)(CR$^6$R$^7$)$_v$NR$^4$R$^5$, —C(=NR$^4$)NR$^4$C(O)R$^6$, —NR$^4$(CR$^6$R$^7$)$_v$Heteroaryl, and —O(CR$^6$R$^7$)$_v$NR$^4$R$^5$.

9. The compound of claim 1, wherein two Y groups, together with the atoms to which they are attached form a pyrrolidine ring.

10. The compound of claim 1, wherein p is 1 or 2.

11. The compound of claim 1, wherein each R$^4$ and R$^5$ are independently selected from the group consisting of hydrogen, optionally substituted C$_1$-C$_6$ alkyl, optionally substituted alkoxyalkyl, optionally substituted hydroxyalkyl, and optionally substituted heterocyclyl.

12. The compound of claim 1, wherein R$^3$ is H, optionally substituted C$_1$-C$_{12}$ alkyl, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, optionally substituted or alkyl-[1,3]dioxol-2-one.

13. The compound of claim 1, wherein R$^3$ is H.

14. The compound of claim 1, wherein R$^3$ is selected from the group consisting of —R$^{30}$OC(O)R$^{31}$, —R$^{30}$OC(O)OR$^{31}$, —R$^{30}$OC(O)NHR$^{31}$, and —R$^{30}$OC(O)N(R$^{31}$)$_2$.

15. The compound of claim 1, wherein R$^3$ is selected from the group consisting of:

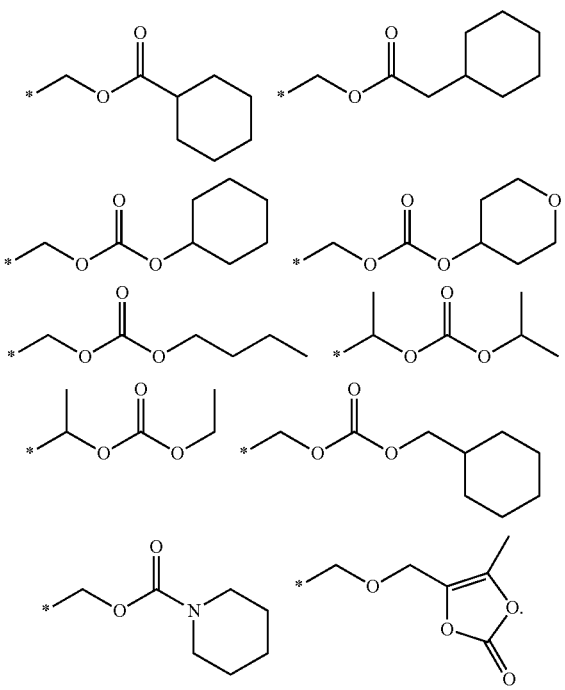

16. The compound of claim 1, wherein the compound is selected from the group represented by the following structures:

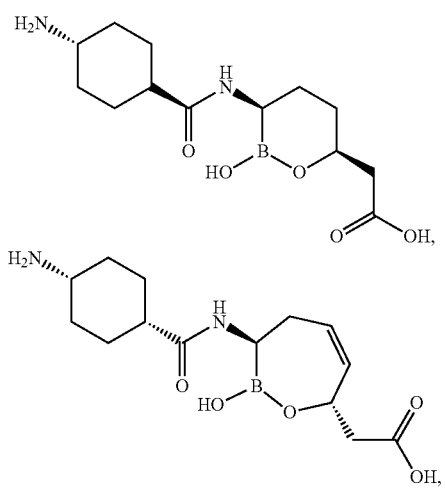

or a pharmaceutically acceptable salt, N-oxide, or isomer thereof.

17. A pharmaceutical composition comprising a compound of claim 1, or a pharmaceutically acceptable salt, N-oxide, or isomer thereof; and a pharmaceutically acceptable excipient.

18. The pharmaceutical composition of claim 17, further comprising a beta-lactam antibiotic.

19. The pharmaceutical composition of claim 18, wherein the beta-lactam antibiotic is a penicillin, cephalosporin, carbapenem, monobactam, bridged monobactam, or a combination thereof.

20. A method of treating a bacterial infection in a subject, comprising administering to the subject a pharmaceutical composition of claim 17, optionally in combination with a beta-lactam antibiotic.

* * * * *